US008435296B2

(12) United States Patent
Kadaba et al.

(10) Patent No.: US 8,435,296 B2
(45) Date of Patent: May 7, 2013

(54) HYDRAULICALLY ACTUATED EXPANDING SPINE CAGE WITH EXTENDABLE LOCKING ANCHOR

(75) Inventors: Murali Kadaba, Emerald Hills, CA (US); Philip J. Simpson, Escondido, CA (US); John E. Ashley, Danville, CA (US); Walter Dean Gillespie, Carlsbad, CA (US); Thomas Grotz, Novato, CA (US); George A. Mansfield, III, San Diego, CA (US); David G. Matsuura, Encinitas, CA (US); Rudy Pretti, Auburn, CA (US)

(73) Assignee: CoAlign Innovations, Inc., Brisbane, CA (US)

( * ) Notice: Subject to any disclaimer, the term of this patent is extended or adjusted under 35 U.S.C. 154(b) by 599 days.

(21) Appl. No.: 12/548,260

(22) Filed: Aug. 26, 2009

(65) Prior Publication Data

US 2010/0057204 A1 Mar. 4, 2010

Related U.S. Application Data

(63) Continuation-in-part of application No. 12/380,840, filed on Mar. 4, 2009, now abandoned, and a continuation-in-part of application No. 12/072,044, filed on Feb. 22, 2008.

(60) Provisional application No. 61/201,518, filed on Dec. 10, 2008.

(51) Int. Cl.
*A61F 2/44* (2006.01)
(52) U.S. Cl.
USPC .................... 623/17.12; 623/17.15

(58) Field of Classification Search ............... 623/17.11, 623/17.12, 17.13, 17.15
See application file for complete search history.

(56) References Cited

U.S. PATENT DOCUMENTS

| 3,875,595 A | 4/1975 | Froning |
| 4,932,975 A | 6/1990 | Main et al. |

(Continued)

FOREIGN PATENT DOCUMENTS

| EP | 1415624 | 5/2004 |
| EP | 1442715 | 8/2004 |

(Continued)

OTHER PUBLICATIONS

International Search Report and Written Opinion dated Sep. 22, 2011 in related International Application No. PCT/US2011/037929.

(Continued)

*Primary Examiner* — Andrew Yang
(74) *Attorney, Agent, or Firm* — Downs Rachlin Martin PLLC

(57) ABSTRACT

A spinal implant which is configured to be deployed between adjacent vertebral bodies. The implant has at least one extendable support element with a retracted configuration to facilitate deployment of the implant and an extended configuration so as to expand the implant and effectively distract the disc space, stabilize the motion segments and eliminate pathologic spine motion. Angular deformities can also be corrected, and natural curvatures restored. Preferably, the implant has a minimal dimension in its unexpanded state that is smaller than the dimensions of the neuroforamen through which it typically passes to be deployed within the intervertebral space. The implant is provided with a locking system preferably having a plurality of locking elements to lock the implant in an extended configuration. Bone engaging anchors also may be provided to ensure secure positioning.

59 Claims, 26 Drawing Sheets

U.S. PATENT DOCUMENTS

| | | | |
|---|---|---|---|
| 4,969,888 | A | 11/1990 | Scholten et al. |
| 5,236,460 | A | 8/1993 | Barber |
| 5,653,763 | A | 8/1997 | Errico et al. |
| 5,665,122 | A | 9/1997 | Kambin |
| 5,827,328 | A | 10/1998 | Buttermann |
| 5,865,848 | A | 2/1999 | Baker |
| 5,980,522 | A | 11/1999 | Koros et al. |
| 6,039,761 | A | 3/2000 | Li et al. |
| 6,102,950 | A | 8/2000 | Vaccaro |
| 6,127,597 | A | 10/2000 | Beyar et al. |
| 6,176,881 | B1 | 1/2001 | Schar et al. |
| 6,193,756 | B1 | 2/2001 | Studer et al. |
| 6,296,665 | B1 | 10/2001 | Strnad et al. |
| 6,371,989 | B1 | 4/2002 | Chauvin et al. |
| 6,375,682 | B1 | 4/2002 | Fleischmann et al. |
| 6,375,683 | B1 * | 4/2002 | Crozet et al. ............... 623/17.15 |
| 6,395,032 | B1 | 5/2002 | Gauchet |
| 6,454,806 | B1 | 9/2002 | Cohen et al. |
| 6,692,495 | B1 | 2/2004 | Zacouto |
| 6,719,796 | B2 | 4/2004 | Cohen et al. |
| 6,723,126 | B1 | 4/2004 | Berry |
| 6,730,088 | B2 | 5/2004 | Yeh |
| 6,764,491 | B2 | 7/2004 | Frey et al. |
| 6,875,235 | B2 | 4/2005 | Ferree |
| 6,981,989 | B1 | 1/2006 | Fleischmann et al. |
| 7,001,431 | B2 | 2/2006 | Bao et al. |
| 7,018,415 | B1 | 3/2006 | McKay |
| 7,018,416 | B2 | 3/2006 | Hanson et al. |
| 7,060,073 | B2 | 6/2006 | Frey et al. |
| 7,094,257 | B2 | 8/2006 | Mujwid et al. |
| 7,166,110 | B2 | 1/2007 | Yundt |
| 7,204,853 | B2 | 4/2007 | Gordon et al. |
| 7,214,243 | B2 | 5/2007 | Taylor |
| 7,217,293 | B2 | 5/2007 | Branch, Jr. |
| 7,282,063 | B2 | 10/2007 | Cohen et al. |
| 7,291,150 | B2 | 11/2007 | Graf |
| 7,291,158 | B2 | 11/2007 | Crow et al. |
| 7,316,686 | B2 | 1/2008 | Dorchak et al. |
| 7,316,714 | B2 | 1/2008 | Gordon et al. |
| 7,351,261 | B2 | 4/2008 | Casey |
| 7,670,359 | B2 | 3/2010 | Yundt |
| 7,722,674 | B1 | 5/2010 | Grotz |
| 7,794,501 | B2 * | 9/2010 | Edie et al. .................. 623/17.12 |
| 7,819,921 | B2 | 10/2010 | Grotz |
| 7,854,766 | B2 | 12/2010 | Moskowitz et al. |
| 7,985,256 | B2 | 7/2011 | Grotz et al. |
| 2002/0128716 | A1 | 9/2002 | Cohen et al. |
| 2002/0138146 | A1 | 9/2002 | Jackson |
| 2002/0151976 | A1 | 10/2002 | Foley et al. |
| 2003/0114899 | A1 | 6/2003 | Woods et al. |
| 2004/0088054 | A1 | 5/2004 | Berry |
| 2004/0133273 | A1 | 7/2004 | Cox |
| 2005/0043800 | A1 | 2/2005 | Paul et al. |
| 2005/0085910 | A1 | 4/2005 | Sweeney |
| 2005/0113842 | A1 | 5/2005 | Bertagnoli et al. |
| 2005/0197702 | A1 | 9/2005 | Coppes et al. |
| 2005/0216084 | A1 | 9/2005 | Fleischmann et al. |
| 2005/0229433 | A1 | 10/2005 | Cachia |
| 2005/0273169 | A1 | 12/2005 | Purcell |
| 2005/0273170 | A1 | 12/2005 | Navarro et al. |
| 2005/0273171 | A1 | 12/2005 | Gordon et al. |
| 2006/0036259 | A1 | 2/2006 | Carl et al. |
| 2006/0085073 | A1 | 4/2006 | Raiszadeh |
| 2006/0106416 | A1 | 5/2006 | Raymond et al. |
| 2006/0116767 | A1 | 6/2006 | Magerl et al. |
| 2006/0149377 | A1 | 7/2006 | Navarro et al. |
| 2006/0167547 | A1 | 7/2006 | Suddaby |
| 2006/0200244 | A1 | 9/2006 | Assaker |
| 2006/0235426 | A1 | 10/2006 | Lim et al. |
| 2006/0235535 | A1 | 10/2006 | Ferree et al. |
| 2006/0264968 | A1 | 11/2006 | Frey et al. |
| 2007/0050030 | A1 | 3/2007 | Kim |
| 2007/0050033 | A1 | 3/2007 | Reo et al. |
| 2007/0073395 | A1 | 3/2007 | Baumgartner et al. |
| 2007/0093901 | A1 | 4/2007 | Grotz et al. |
| 2007/0093903 | A1 | 4/2007 | Cheng |
| 2007/0123987 | A1 | 5/2007 | Bernstein |
| 2007/0179611 | A1 | 8/2007 | DiPoto et al. |
| 2007/0233254 | A1 | 10/2007 | Grotz et al. |
| 2007/0255409 | A1 | 11/2007 | Dickson et al. |
| 2007/0255413 | A1 | 11/2007 | Edie et al. |
| 2007/0255415 | A1 | 11/2007 | Edie et al. |
| 2007/0288092 | A1 | 12/2007 | Bambakidis |
| 2008/0058930 | A1 | 3/2008 | Edie et al. |
| 2008/0065082 | A1 | 3/2008 | Chang et al. |
| 2008/0077150 | A1 | 3/2008 | Nguyen |
| 2008/0103601 | A1 | 5/2008 | Biro et al. |
| 2008/0114467 | A1 | 5/2008 | Capote et al. |
| 2008/0147194 | A1 | 6/2008 | Grotz et al. |
| 2008/0161933 | A1 | 7/2008 | Grotz et al. |
| 2008/0177387 | A1 | 7/2008 | Parimore et al. |
| 2008/0281424 | A1 | 11/2008 | Parry et al. |
| 2008/0300598 | A1 | 12/2008 | Barreiro et al. |
| 2009/0043312 | A1 | 2/2009 | Koulisis et al. |
| 2009/0204215 | A1 | 8/2009 | McClintock et al. |
| 2009/0216331 | A1 | 8/2009 | Grotz et al. |
| 2009/0222100 | A1 | 9/2009 | Cipoletti et al. |
| 2009/0270987 | A1 | 10/2009 | Heinz et al. |
| 2010/0057204 | A1 | 3/2010 | Kadaba |
| 2010/0145455 | A1 | 6/2010 | Simpson et al. |
| 2011/0130835 | A1 | 6/2011 | Ashley et al. |
| 2011/0270398 | A1 | 11/2011 | Grotz et al. |
| 2011/0288646 | A1 | 11/2011 | Moskowitz et al. |
| 2012/0245695 | A1 | 9/2012 | Simpson et al. |

FOREIGN PATENT DOCUMENTS

| | | |
|---|---|---|
| WO | 2004016250 | 2/2004 |
| WO | 2008011371 | 1/2008 |
| WO | 2008039811 | 4/2008 |
| WO | 2008121251 | 10/2008 |
| WO | 2009105182 | 8/2009 |
| WO | 2010068725 | 6/2010 |
| WO | 2011150077 | 12/2011 |

OTHER PUBLICATIONS

Final Office Action dated Nov. 18, 2011 in related U.S. Appl. No. 12/072,044, filed Feb. 22, 2008.

Response to Office Action filed Nov. 18, 2011 in related U.S. Appl. No. 12/384,622, filed Apr. 7, 2009.

Related U.S. Appl. No. 11/535,432, filed Sep. 26, 2006, in the name of Thomas Grotz et al., titled ,"Selectively Expanding Spine Cage, Hydraulically Controllable in Three Dimensions for Enhanced Spinal Fusion."

Related U.S. Appl. No. 12/787,281, filed, May 25, 2010, in the name of John E. Ashley et al., titled "Adjustable Distraction Cage with Linked Locking Mechanism."

Related U.S. Appl. No. 12/380,840, filed Mar. 4, 2009, in the name of Philip J. Simpson et al., titled "Lockable Spinal Implant."

Related International Application No. PCT/US2009/067446 filed Dec. 10, 2009, in the name of Innvotec Surgical, Inc., titled "Lockable Expanding Spine Cage."

International Search Report and Written Opinion dated Aug. 13, 2010, in related International Application No. PCT/US2009/067446 filed Dec. 10, 2009.

Related International Application No. PCT/US2009/00974 filed Feb. 17, 2009, in the name of Innvotec Surgical, Inc., titled "Spinal Implant with Expandable Fixation."

International Search Report and Written Opinion dated May 6, 2009, in related International Application No. PCT/US2009/000974 filed Feb. 17, 2009.

Related International Application No. PCT/US2008/003776 filed Mar. 21, 2008, in the name of Innvotec Surgical, Inc., titled "Selectively Expanding Spine Cage, Hydraulically Controllable in Three Dimensions for Vertebral Body Replacement."

International Search Report and Written Opinion dated Jun. 30, 2009, in related International Application No. PCT/US2008/003776 filed Mar. 21, 2008.

Related U.S. Appl. No. 11/692,800, filed Mar. 28, 2007, in the name of R. Thomas Grotz et al., titled "Selectively Expanding Spine Cage, Hydraulically Controllable in Three Dimensions for Vertebral Body Replacement."

Office Action dated Sep. 16, 2010 in related U.S. Appl. No. 11/692,800, filed Mar. 28, 2007, in the name of R. Thomas Grotz et al., titled "Selectively Expanding Spine Cage, Hydraulically Controllable in Three Dimensions for Vertebral Body Replacement.".

Related U.S. Appl. No. 12/072,044, filed Feb. 22, 2008, in the name of R. Thomas Grotz et al., titled "Spinal Implant with Expandable Fixation."

Related U.S. Appl. No. 11/981,452, filed Oct. 31, 2007, in the name of R. Thomas Grotz et al., titled "Selectively Expanding Spine Cage, Hydraulically Controllable in Three Dimensions for Vertebral Body Replacement."

Related U.S. Appl. No. 11/981,150, filed Oct. 31, 2007, in the name of R. Thomas Grotz et al., titled "Selectively Expanding Spine Cage, Hydraulically Controllable in Three Dimensions for Vertebral Body Replacement."

Related U.S. Appl. No. 12/384,622, filed Apr. 7, 2009, in the name of Philip J. Simpson et al., titled "Lockable Spinal Implant."

Preliminary Amendment dated Dec. 4, 2007 in related U.S. Appl. No. 11/535,432, titled "Selectively Expanding Spine Cage, Hydraulically Controllable in Three Dimensions for Enhanced Spinal Fusion."

Second Preliminary Amendment dated Mar. 18, 2008 in related U.S. Appl. No. 11/535,432, titled "Selectively Expanding Spine Cage, Hydraulically Controllable in Three Dimensions for Enhanced Spinal Fusion."

Third Preliminary Amendment dated Aug. 7, 2008 in related U.S. Appl. No. 11/535,432, titled "Selectively Expanding Spine Cage, Hydraulically Controllable in Three Dimensions for Enhanced Spinal Fusion."

Restriction Requirement dated Mar. 17, 2010 in related U.S. Appl. No. 11/535,432, titled "Selectively Expanding Spine Cage, Hydraulically Controllable in Three Dimensions for Enhanced Spinal Fusion."

Response to Restriction Requirement dated Mar. 31, 2010 in related U.S. Appl. No. 11/535,432, titled "Selectively Expanding Spine Cage, Hydraulically Controllabe in Three Dimensions For Enhanced Spinal Fusion."

Office Action dated Jul. 9, 2010 in related U.S. Appl. No. 11/535,432, titled "Selectively Expanding Spine Cage, Hydraulically Controllable in Three Dimensions for Enhanced Spinal Fusion."

Response to Office Action dated Oct. 4, 2010 in related U.S. Appl. No. 11/535,432, titled "Selectively Expanding Spine Cage, Hydraulically Controllable in Three Dimensions for Enhanced Spinal Fusion."

Preliminary Amendment dated Oct. 31, 2007 in related U.S. Appl. No. 11/981,452, filed Oct. 31, 2007, titled "Selectively Expanding Spine Cage, Hydraulically Controllable in Three Dimensions for Vertebral Body Replacement."

Preliminary Amendment dated Oct. 31, 2007 in related U.S. Appl. No. 11/981,150, filed Oct. 31, 2007, titled "Selectively Expanding Spine Cage, Hydraulically Controllable in Three Dimensions for Vertebral Body Replacement."

International Search Report and Written Opinion dated Apr. 10, 2008, in related International Application No. PCT/ US2007/079474.

Examination Report dated Oct. 18, 2011 in related EU Application No. 08727082.3 in the name of CoAlign Innovations, Inc.

Final Office Action dated Mar. 2, 2011, in related U.S. Appl. No. 11/692,800 entitled "Selectively Expanding Spine Cage, Hydraulically Controllable in Three Dimensions for Vertebral Body Replacement."

Response to Final Office Action dated Mar. 23, 2011, in related U.S. Appl. No. 11/535,432 entitled "Selectively Expanding Spine Cage, Hydraulically Controllable in Three Dimensions for Enhanced Spinal Fusion."

Office Action dated May 9, 2011, in related U.S. Appl. No. 12/072,044 entitled "Spinal Implant With Expandable Fixation."

Response to Restriction Requirement dated Jun. 6, 2011, in related U.S. Appl. No. 12/384,622 entitled "Lockable Spinal Implant."

Related International Application No. PCT/US2011/037929 filed May 25, 2011, entitled "Adjustable Distraction Cage With Linked Locking Mechanisms."

Office Action dated Apr. 26, 2011, in related CN Application No. 200880016846.7, entitled "Selectively Expanding Spine Cage, Hydraulically Controllable in Three Dimensions for Vertebral Body Replacement."

Response to Office Action dated Jul. 5, 2011, in related U.S. Appl. No. 11/981,150, entitled "Selectively Expanding Spine Cage, Hydraulically Controllable in Three Dimensions for Enhanced Spinal Fusion."

Advisory Action dated May 19, 2011, in related U.S. Appl. No. 11/692,800, entitled "Selectively Expanding Spine Cage, Hydraulically Controllable in Three Dimensions for Vertebral Body Replacement."

Amendment After Final Office Action dated Jul. 5, 2011, in related U.S. Appl. No. 11/692,800, entitled "Selectively Expanding Spine Cage, Hydraulically Controllable in Three Dimensions for Vertebral Body Replacement."

Related U.S. Appl. No. 13/183,080, filed Jul. 14, 2011, in the name of Thomas Grotz et al., entitled "Selectively Expanding Spine Cage, Hydraulically Controllable in Three Dimensions for Enhanced Spinal Fusion."

Notice of Allowance dated Aug. 3, 2011, in related U.S. Appl. No. 11/692,800, entitled "Selectively Expanding Spine Cage, Hydraulically Controllable in Three Dimensions for Vertebral Body Replacement."

Response to Office Action dated Aug. 9, 2011, in related U.S. Appl. No. 12/072,044, entitled "Spinal Implant With Expandable Fixation."

Office Action dated Aug. 31, 2011, in related U.S. Appl. No. 12/384,622, entitled "Lockable Spinal Implant."

Office Action dated Apr. 5, 2011, in related U.S. Appl. No. 11/981,150 entitled "Selectively Expanding Spine Cage, Hydraulically Controllable in Three Dimensions for Enhanced Spinal Fusion."

Office Action dated Mar. 31, 2011, in related U.S. Appl. No. 11/981,452 entitled "Selectively Expanding Spine Cage, Hydraulically Controllable in Three Dimensions for Vertebral Body Replacement."

Restriction Requirement dated Apr. 4, 2011, in related U.S. Appl. No. 12/384,622 entitled "Lockable Spinal Implant."

Notice of Allowance dated Apr. 13, 2011, in related U.S. Appl. No. 11/535,432, entitled "Selectively Expanding Spine Cage, Hydraulically Controllable in Three Dimensions for Enhanced Spinal Fusion."

Restriction Requirement dated May 2, 2011, in related U.S. Appl. No. 12/380,840 entitled "Lockable Spinal Implant."

Response to Final Office Action dated May 2, 2011, in related U.S. Appl. No. 11/692,800 entitled "Selectively Expanding Spine Cage, Hydraulically Controllable in Three Dimensions for Vertebral Body Replacement."

Office Action dated Apr. 9, 2012, in related U.S. Appl. No. 12/787,281, filed May 25, 2010.

Notice of Allowance dated Feb. 23, 2012, in related U.S. Appl. No. 12/384,622, filed Apr. 7, 2009.

Restriction Requirement dated Feb. 27, 2012, in related U.S. Appl. No. 12/787,281, filed May 25, 2010.

Response to Restriction Requirement dated Mar. 27, 2012, in related U.S. Appl. No. 12/787,281, filed May 25, 2010.

Response to Office Action dated Feb. 17, 2012, in related U.S. Appl. No. 12/072,044, filed Feb. 22, 2008.

Advisory Action dated Mar. 12, 2012, in related U.S. Appl. No. 12/072,044, filed Feb. 22, 2008.

Response to Final Office Action dated Mar. 19, 2012, in related U.S. Appl. No. 12/072,044, filed Feb. 22, 2008.

Office Action dated Mar. 29, 2012, in related U.S. Appl. No. 12/072,044, filed Feb. 22, 2008.

Response to Office Action dated Dec. 16, 2010, in related U.S. Appl. No. 11/692,800 entitled "Selectively Expanding Spine Cage, Hydraulically Controllable in Three Dimensions for Vertebral Body Replacement."

Terminal Disclaimer dated Dec. 16, 2010, in related U.S. Appl. No. 11/692,800 entitled "Selectively Expanding Spine Cage, Hydraulically Controllable in Three Dimensions for Vertebral Body Replacement."

Restriction Requirement dated Dec. 27, 2010, in related U.S. Appl. No. 12/072,044 entitled "Spinal Implant With Expandable Fixation."

Amendment and Response to Restriction Requirement dated Jan. 27, 2011, in related U.S. Appl. No. 12/072,044 entitled "Spinal Implant With Expandable Fixation."

International Search Report and Written Opinion dated Nov. 11, 2010, in International Application No. PCT/US2010/031247 entitled "Insertion Handle for Implant."

Final Office Action dated Feb. 1, 2011, in related U.S. Appl. No. 11/535,432 entitled "Selectively Expanding Spine Cage, Hydraulically Controllable in Three Dimensions for Enhanced Spinal Fusion."

Translated Second Office Action dated Apr. 26, 2012 in related China Application No. 200880016846.7.

Office Action dated Jun. 20, 2012, in related U.S. Appl. No. 13/183,080, filed Jul. 14, 2011.

Office Action dated Jun. 20, 2012, in related U.S. Appl. No. 13/311,487, filed Dec. 5, 2011.

Final Office Action dated Jun. 19, 2012, in related U.S. Appl. No. 11/981,150, filed Oct. 31, 2007.

Response to Office Action dated Jul. 30, 2012, in related U.S. Appl. No. 12/072,044, filed Feb. 22, 2008.

Examination Report dated Jul. 17, 2012, in European Patent Application No. 09712948.0.

Response to Office Action dated Oct. 9, 2012, in related U.S. Appl. No. 12/787,281, filed May 25, 2010.

Response to Final Office Action dated Oct. 18, 2012, in connection with related U.S. Appl. No. 11/981,150, filed Oct. 31, 2007.

Notice of Allowance dated Nov. 9, 2012, in connection with related U.S. Appl. No. 11/981,150, filed Oct. 31, 2007.

Response to Office Action dated Oct. 22, 2012, in connection with related U.S. Appl. No. 13/311,487, filed Dec. 5, 2011.

Response to Office Action dated Oct. 9, 2012, in connection with related U.S. Appl. No. 12/787,281, filed May 25, 2010.

Final Office Action dated Jan. 2, 2013, in connection with related U.S. Appl. No. 12/787,281, filed May 25, 2010.

Final Office Action dated Nov. 19, 2012, in connection with related U.S. Appl. No. 12/072,044, filed Feb. 22, 2008.

Response to Office Action dated Oct. 22, 2012, in connection with related U.S. Appl. No. 13/183,080, filed Jul. 14, 2011.

* cited by examiner

HYDRAULICALLY ACTUATED EXPANDING SPINE CAGE WITH EXTENDABLE LOCKING ANCHOR

RELATED APPLICATION DATA

This application is a continuation-in-part of U.S. Nonprovisional patent application Ser. No. 12/380,840, filed on Mar. 4, 2009, entitled "Lockable Spinal Implant," which is a nonprovisional of U.S. Provisional Patent Application Ser. No. 61/201,518, filed on Dec. 10, 2008, entitled "Lockable Spinal Implant." This application is also a continuation-in-part of U.S. Nonprovisional patent application Ser. No. 12/072,044, filed Feb. 22, 2008, entitled "Spinal Implant With Expandable Fixation."

This application is also related to U.S. patent application Ser. No. 11/692,800, filed Mar. 28, 2007, entitled "Selectively Expanding Spine Cage, Hydraulically Controllable in Three Dimensions for Vertebral Body Replacement," which is a continuation-in-part of U.S. Nonprovisional patent application Ser. No. 11/535,432, filed Sep. 26, 2006, entitled "Selectively Expanding Spine Cage, Hydraulically Controllable in Three Dimensions for Enhanced Spinal Infusion," which is a nonprovisional of U.S. Provisional Patent Application Ser. No. 60/720,784, filed Sep. 26, 2005, entitled "Selectively Expanding Spine Cage, Hydraulically Controllable in Three Dimensions for Enhanced Spinal Infusion."

Each of the above listed applications is incorporated herein by reference in its entirety.

FIELD OF THE INVENTION

The invention relates to devices and methods for stabilizing the vertebral motion segment. More specifically, the field of the invention relates to an expandable spinal implant with locking elements configured to lock the implant in an expanded configuration within an intervertebral space to provide controlled spinal correction in three dimensions for improved spinal intervertebral body distraction and fusion.

BACKGROUND

A conventional spine cage or implant is characterized by a kidney bean shaped body which is typically inserted posteriorly through the neuroforamen of the distracted spine after a trial implant creates a pathway. Existing devices for interbody stabilization have important and significant limitations, including inability to expand and distract the endplates or to fix the device in place to prevent relative movement between the device and an adjacent vertebral body. Current devices for interbody stabilization include static spacers composed of titanium, PEEK, and high performance thermoplastic polymer produced by VICTREX, (Victrex USA Inc, 3A Caledon Court; Greenville, S.C. 29615), carbon fiber, or resorbable polymers. Moreover, current interbody spacers do not maintain interbody lordosis and can contribute to the formation of a straight or even kyphotic segment and the clinical problem of "flatback syndrome." Separation of vertebral endplates increases space available for the neural elements, specifically the neural foramen. Existing static cages do not reliably improve space for the neural elements. Therefore, what is needed is a spinal implant that will provide space for the neural elements posteriorly between the vertebral bodies, or at least maintain the natural bone contours to avoid neuropraxia (nerve stretch) or encroachment.

Conventional devices for intervertebral body stabilization includes poor interface between bone and the biomaterial of the device. Conventional static interbody spacers form a weak interface between bone and biomaterial. Although the surface of such implants is typically provided with a series of ridges or coated with hydroxyapetite, the ridges may be in parallel with applied horizontal vectors or side-to-side motion. That is, the ridges or coatings on the implant offer little resistance to movement applied to either side of the endplates. Thus, nonunion is common in allograft, titanium and polymer spacers, due to motion between the implant and host bone.

SUMMARY OF THE DISCLOSURE

This invention is generally directed to a spinal implant for insertion between superior and second vertebral end plates after partial or total removal of a spinal disc. The spinal implant embodying features of the invention has a contracted configuration for easy installation between adjacent vertebral bodies and an expanded configuration to support the vertebrae in a desirable position. More specifically, the implant has a plurality of inter-engagable elements which locks the implant in an expanded configuration to hold the vertebral or joint sections in the desired positions.

The invention is particularly directed to a spinal implant suitable for placement between superior and interior vertebral bodies. The spinal implant has a first member or top plate for engaging an end of the superior vertebral body and a second member or base for engaging an end of the inferior vertebral body and has one or more extendable support elements preferably with one or more top end plates that engage vertebral bodies in the expanded configuration. The one or more extendable support elements have a first contracted configuration to facilitate deployment of the implant between the superior and inferior vertebral bodies and safely past sensitive neural elements and a second or an extended configuration to engage the end plates of the vertebral bodies. The implant has a locking system which has a locking element that mechanically engages or interlocks with the extendable support element or the first member to lock the implant between the superior and inferior vertebral bodies in an expanded configuration.

The extendable support element(s) may be extended in a variety of ways such as with fluid pressure, e.g. hydraulic fluid or gas, by mechanical force, such as a threaded connection with a rotating driving member or other suitable means. Fluidic displacement is preferred. The extendable support element(s) are disposed in cylinders which support and guide the extendable support elements when they are extended. However, the locking system is separate from the extendable support member and cylinder receiving the supporter member, although the extending support member may initiate the locking system and the support member and cylinder may have lock support members attached thereto.

In one presently preferred system, the spinal implant having features of the invention comprises an inferior pressure applying member or base with a first bone engaging surface, one or more extendable support members cooperating with the base and a superior pressure applying member such as a top end plate with a second bone engaging surface that is coupled to the at least one extendable member. The spinal implant preferably has a plurality of engaging locking elements that are configured to independently lock one or more of the extendable support members or pressure applying members in an extended configuration to thereby provide desired disc height between adjacent vertebrae and in some instances to provide a desired corrective spinal alignment in a plurality of dimensions.

The spinal implant or selectively expanding spine cage (SEC) embodying features of the invention is particularly suitable for posterior or transforaminal insertion between superior and inferior vertebral end plates as described in copending application Ser. No. 11/535,432, filed Sep. 26, 2006, and Ser. No. 11/692,800, filed Mar. 28, 2007. The implant has a contracted or unexpanded configuration which allows easy deployment and is typically about 0.5 to about 1 cm in maximum short transverse dimension so as to enable minimally invasive insertion posteriorly between vertebral pedicles through a working space of approximately 1 cm in diameter.

In one preferred embodiment, the spinal implant for placement between adjacent vertebral bodies as described above has an upper locking member with stepped supporting surfaces on the underside thereof and a lower locking member with stepped supporting surfaces on the top side thereof which are configured to engage the stepped supporting surface of the upper locking member to lock the implant in an extended configuration. Extension of the expandable members or pistons to raise the superior pressure applying member increases longitudinal spacing between the upper and lower locking members. Relative motion, rotational or linear, between the upper and lower locking members causes the stepped supporting surfaces of the lower locking members and the stepped supporting surfaces of the upper locking members to re-engage to fix the locking members in an increased spaced apart relationship and thereby lock the implant in the extended configuration.

Since the vertebral end plates are held together at one end by a ligament much like a clamshell, as the implant expands against the vertebral end plates, the amount of vertical expansion can be adjusted to create the desired anterior/posterior correction angle.

Left and right lateral correction of the spine is achieved by differential vertical expansion of the two or more extendable members of the implant. Each extendable member may be independently controlled by a master cylinder or syringe located ex vivo (away from the patient) for moving the pistons and attached top plate vertical for correcting spinal deformities anteriorly or posteriorly, medial or lateral, thus available to provide spinal correction in three dimensions. See for example U.S. applications copending application Ser. No. 11/535,432, filed Sep. 26, 2006, and Ser. No. 11/692,800, filed Mar. 28, 2007.

A minimally invasive downsized insertion tool, such as described in the above referenced applications, both inserts the unexpanded implant posteriorly and provides the hydraulic or mechanical lines communicating with the interior of the implant. The insertion tool may also provide a line for communicating the liquid or slurry bone graft material into the intervertebral space for subsequent fusion. Advantageously, hydraulic lines are small size tubing to allow for high hydraulic pressure without danger of the lines bursting.

Due to the mechanical advantage provided by a hydraulic system or a proximally operated mechanical system, the implant has minimized size and diameter in its unexpanded state that is smaller than the diameter of a prepared neuroforamen. The implant thus can be inserted transforaminally and engaged between the endplates of the adjacent vertebra to effectively distract the intervertebral area, restore space for neural elements, stabilize the motion segment and eliminate pathologic segmental motion. The implant enhances spine arthrodesis by creating a rigid spine segment.

The implant is preferably provided with a hollow interior to enable a comparatively large quantity of bone growth conductive or inductive agents to be contained therein that through openings communicate directly to adjacent bone. Importantly, this results in fixation forces greater than adjacent bone and soft tissue failure forces. The implant can be used to promote fusion, and/or to correct deformities such as scoliosis, kyphosis, and spondylolisthesis.

The clinical goals of the implant and the method for its insertion provide a minimally invasive risk of trauma to nerve roots, reduce pain, improve function, and permit early mobilization of the patient after fusion surgery. The fixation elements maintain the implant in a desired position until healing (fusion or arthrodesis) occurs. At this point, the implant is incorporated inside bone and its role becomes quiescent.

Thus, a key feature of the invention is that an implant can be inserted posteriorly between vertebral pedicles in only a working space of about ½ cm and then be expanded to about 100% to about 200%, typically about 160%, of its original insertion size and locked in that position to provide a closely controlled full range of permanent spinal correction in three dimensions. These and other advantages of the invention will become more apparent from the following detailed description and the accompanying exemplary drawings.

In other embodiments of the invention, extendable, locking, bone engaging anchors are provided to ensure that the implant is positively engaged with the bone after insertion.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
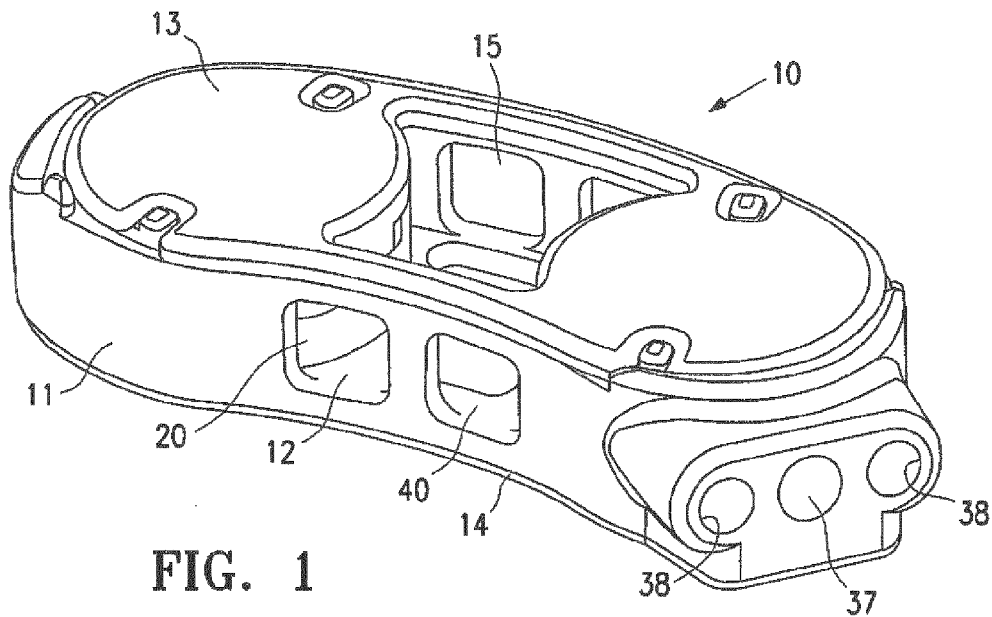
FIG. 1 is a perspective view of an intervertebral implant in a contracted configuration embodying features of the invention.

FIGS. 1-10B Illustrate an example of an intervertebral implant 10, a Selectively Expandable Cage (SEC), having features of the invention. The implant 10 generally includes a housing 11, a housing base 12, an interlocking top endplate 13, a bottom endplate 14, an interior cavity 15 within the housing 11 and a pair of cylinders 16. Upper lock supports 17 are attached to the underside of the top endplate 13 and have multi-stepped lower support surfaces 18 much like an inverted staircase. Lower lock supports 20, having multi-stepped upper support surfaces 21 surround cylinders 16 much like an upright staircase. Pistons 22 are secured to the under surface of top endplate 13. Seal members 23 are slidably disposed within the cylinders 16 and are mounted on pistons 22. The upper surface 24 of bottom end plate 14 is provided with locking actuator channels 25 which partially receive spring locking actuators 26. The base 12 of the housing 11 has arcuate slots 27 which are configured to slidably receive the depending elements 28 or locking actuator transfer element of the lower lock supports 20 and partially receive the spring locking actuators 26. Depending elements 28 engage the forward end 30 of spring locking actuators 26. The spring locking actuators 26 are initially in a compressed configuration so that upon the extension of the top endplate 13 and the attached upper lock supports 17, the lower lock supports 20 rotate about the cylinders 16 due to the force applied by the biased spring locking actuator 26. This causes the lock support surfaces 21 of the lower lock supports 20 to engage support surfaces 18 of the upper lock supports so as to lock the top end plate 13 in an extended configuration. The support surfaces 18 of the upper lock supports 17 and the support surfaces 21 of the lower lock supports 20 are tiered with multiple steps so that the implant 10 can be locked at several different expanded heights. The underside stepped support surfaces 18 of the upper lock support 17 may be provided with increasing riser height (alignment faces 46) in the upward direction to provide smaller incremental expansion near the end of the piston expansion. In addition or alternatively, the stepped support surfaces 21 of the lower lock support 20 may be provided with decreasing riser height in the upward direction for the same reason. A variety of riser heights of the upper lock support 17 or lower lock support 20 can be provided. The lowermost stepped support surface 18 of the upper lock support 17 and the uppermost stepped support surface 21 of the lower lock support 20 may be provided with various lengths and widths to ensure better support.

Figure 2:
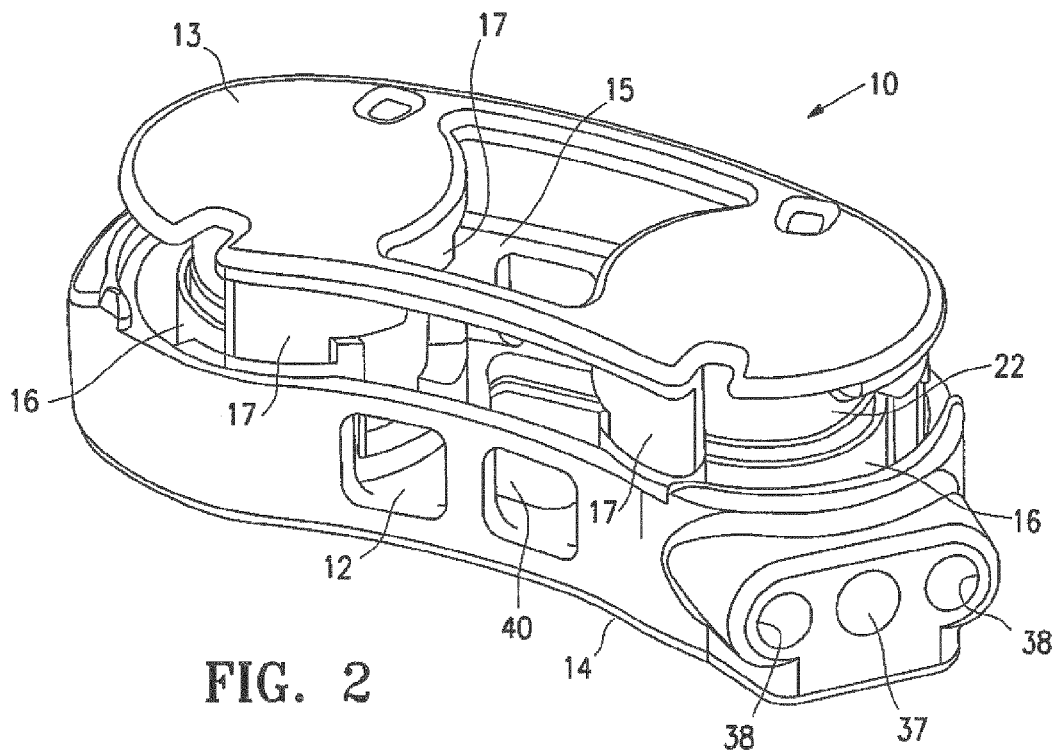
FIG. 2 a perspective view of the implant shown in FIG. 1 in an expanded configuration.

As can be seen in FIG. 2 there are two sets of upper lock supports 17 attached to the top endplate 13 and there are two sets of lower lock supports 20 in this embodiment, but a single set or more than two sets of upper and lower lock supports can also be used to lock the implant 10 in the expanded state.

The implant 10 is configured to be implanted between opposing vertebral bodies in the spine to facilitate bony fusion between those vertebral bodies. The implant 10 is shown in its collapsed or contracted configuration in FIG. 1 and in one example of its expanded configuration in FIG. 2. In the collapsed state, the implant 10 can be inserted easily into the intervertebral body space through a minimal incision and with minimal tissue removal. Once in that space, the implant 10 can be expanded against the two opposing vertebral bodies to distract them and thereby restore height to the intervertebral space. This provides stable opposition of the implant 10 to both vertebral bodies and optimizes the bony fusion process. The fusion process can also be enhanced by filling the interior cavity 15 with autologous bone graft, a bone growth enabling matrix, and/or bone growth stimulating substances prior to and/or after insertion into the body.

Figure 3:
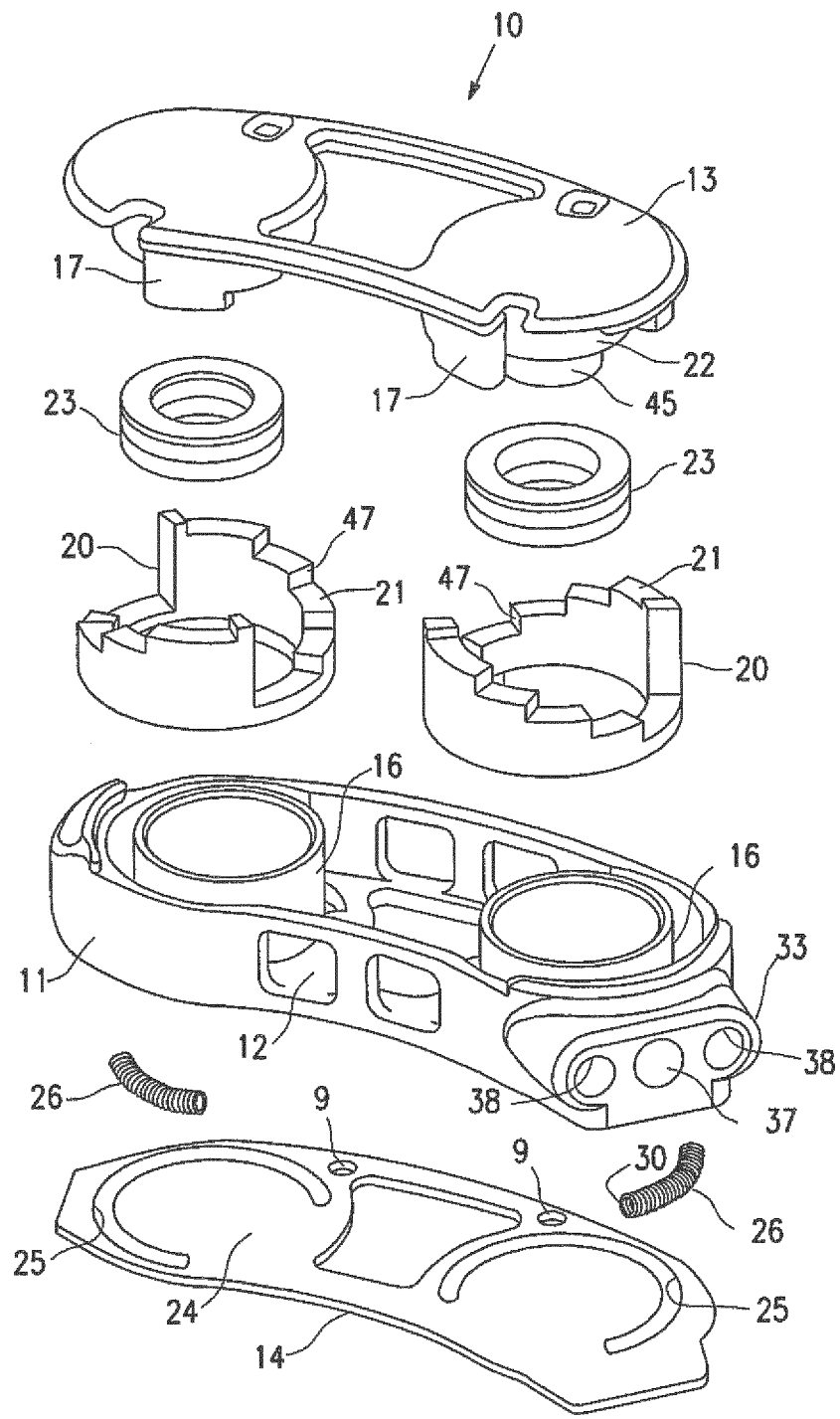
FIG. 3 is an exploded perspective view of the implant shown in FIG. 1.
Figure 4A:
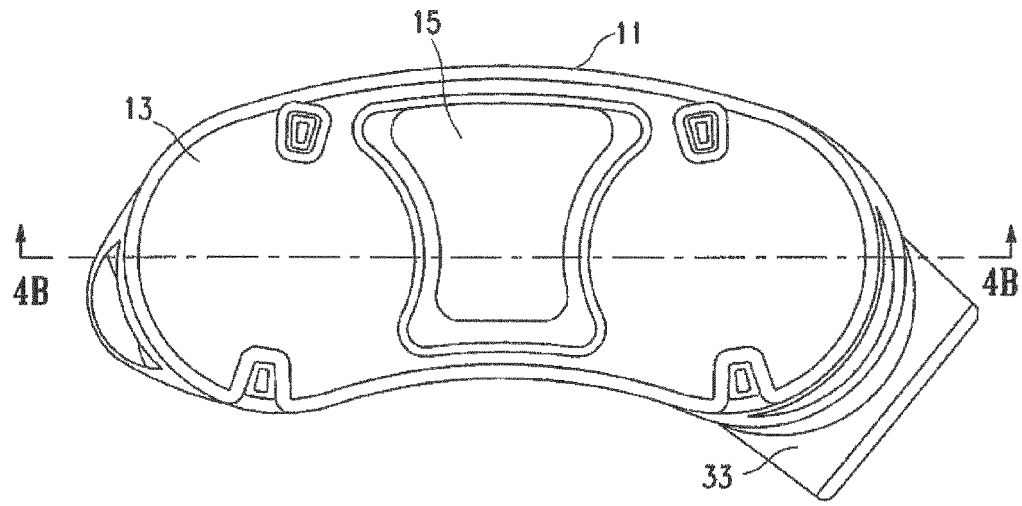
FIG. 4A is a top view of the implant shown in FIG. 1.
Figure 4B:
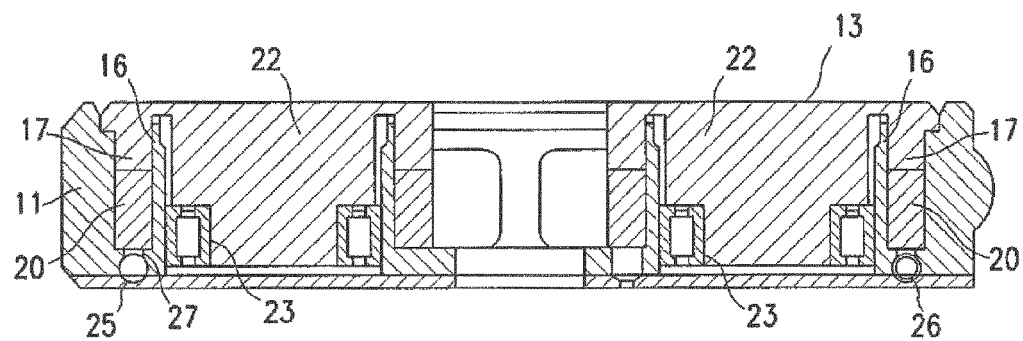
FIG. 4B is a side cross-sectional view through line 4B-4B of the implant shown in FIG. 4A.

Further details of individual parts of the implant 10 are depicted in FIGS. 3, 4A and 4B. Pistons 22 are attached to the underside of the top endplate 13 which are configured to support seal members 23 which run inside of cylinders 16 located in the housing 11. When the cylinders 16 are pressurized as will be described in more detail below, the seals 23 running inside the cylinders 16 and pistons 22 slidably disposed within the seals are vertically displaced, translating the top endplate 13 vertically above the housing 11. Lower lock supports 20 are located around the outer wall of the cylinders 16. When the top endplate 13 is vertically displaced, which in turn displaces the attached upper lock supports 17, the lower lock supports are rotated by the biased locking actuators 26 to a locking position. Arcuate locking actuator channels 25 in the top surface of bottom plate 14 and the arcuate slots 27 in the housing base 12 confines the locking actuators 26 to the housing 11.

Figure 5A:
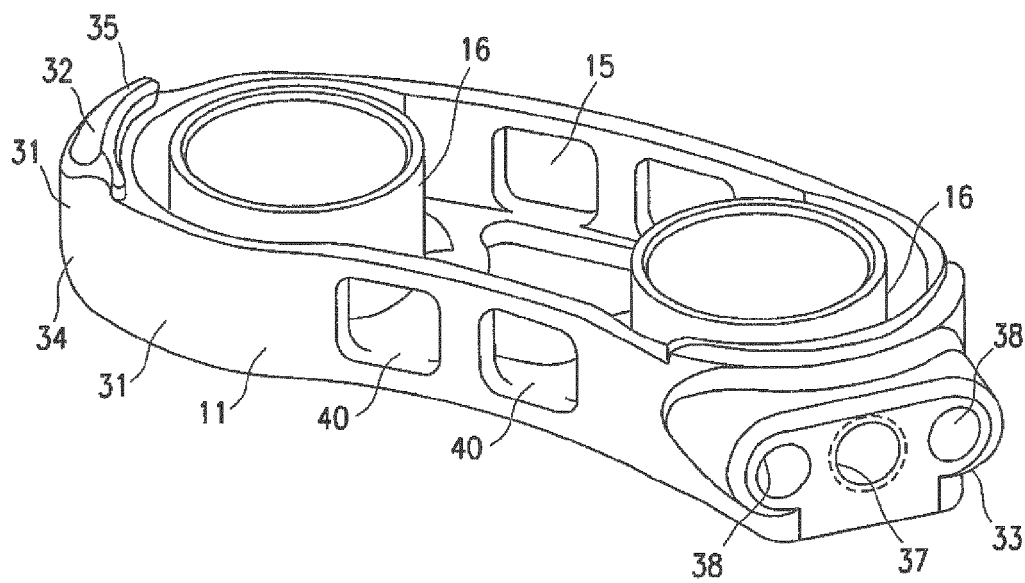
FIG. 5A is a perspective view of a lower part of the implant shown in FIG. 1 with upper portions and bottom face removed.
Figure 5B:
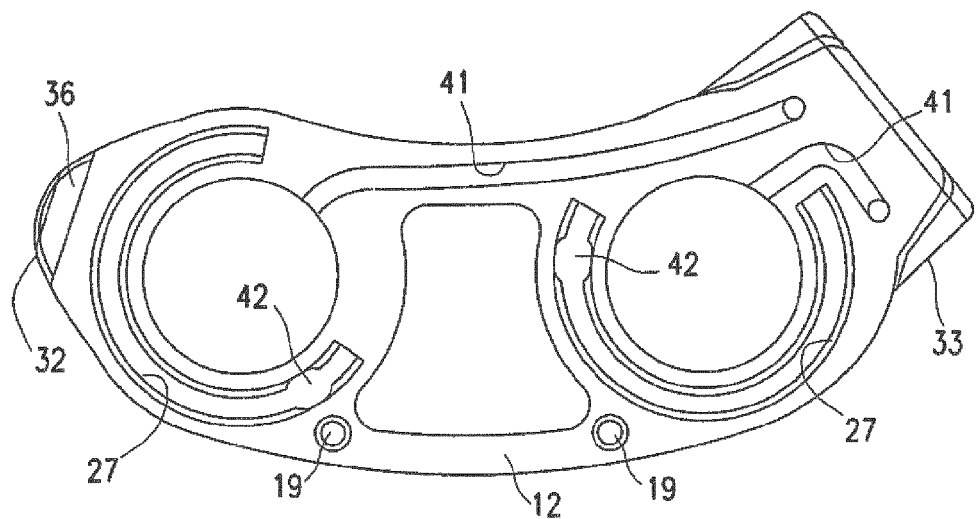
FIG. 5B is a bottom view of the lower portion shown in FIG. 5A.

Additional details of the housing 11 are depicted in FIGS. 5A and 5B. The housing 11 comprises an outer wall 31 and cylinders 16 which are secured to housing base 12. The outer wall 31 supports a leading nose 32 on the distal end and a delivery boss 33 on the proximal end. The leading nose 32 has inwardly directed side tapered faces 34 and top tapered face 35 and bottom tapered face 36. These tapered faces 34, 35 and 36 enable non-traumatic insertion of the implant 10 passed neural elements and between the vertebral bodies. The delivery boss 33 contains a delivery tool anchor 37 which allows secure attachment of the implant 10 to a delivery tool (not shown), which is illustrated in copending application Ser. No. 11/535,432, filed Sep. 26, 2006, and Ser. No. 11/692,800, filed Mar. 28, 2007 for insertion into a vertebral space. The delivery boss 33 also contains pressure input ports 38 which are used to deliver a pressurized fluid to the interiors of cylinders 16. The outer wall 31 of the housing 11 also provides side openings 40 which provide space for bony in-growth into central cavity 15 in the housing 11 and provide radiolucent openings for the radiographic imaging of the process of bony in-growth. The housing base 12 also contains pressure channels 41 which deliver pressurized fluid from the pressure input ports 38 to the interior of cylinders 16. Although the housing base 12 of implant 10 is depicted with independent pressure channel 41 for each cylinder 16, other embodiments can contain one or more branching pressure channels for delivering pressurized fluid to two or more cylinders 16. As previously mentioned, the housing base 12 also has locking actuator slots 27 which hold and guide the locking actuators 26. The locking actuator slots 27 contain a wider portion, locking actuator opening 42, to enable insertion of the locking actuator 26 into the channels defined by the locking actuator slots 27 in housing base 12 and the locking actuator channels 25 in the bottom end plate 14. The housing base 12 also has optional alignment bosses 19 which align the bottom endplate 14 to the housing 11 via optional alignment holes 9.

Figure 6A:
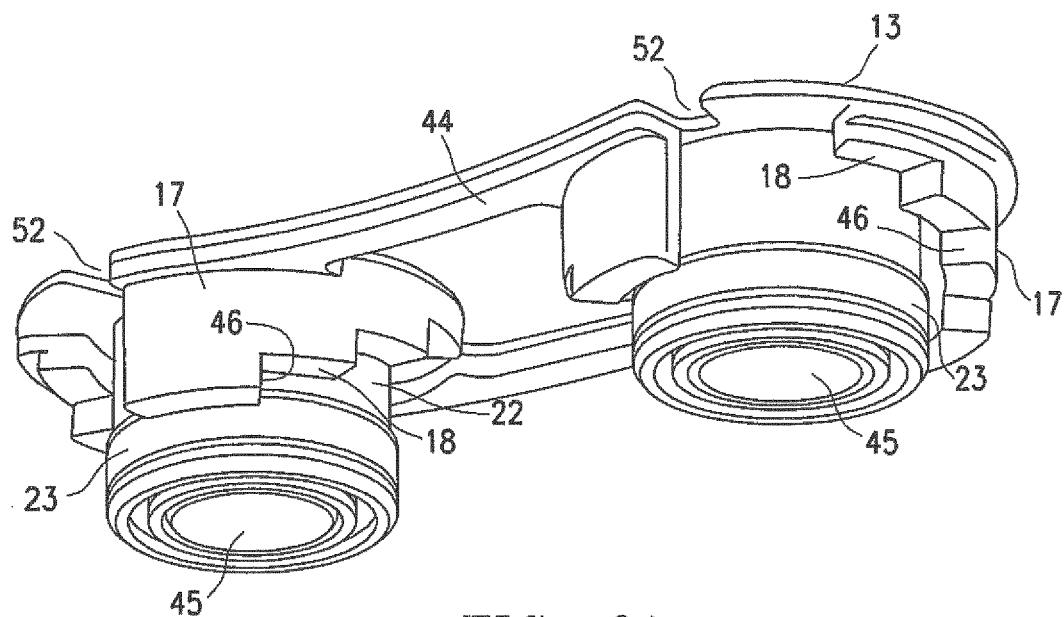
FIG. 6A is a perspective view of the upper portion of the implant shown in FIG. 1 with the lower portion removed.
Figure 6B:
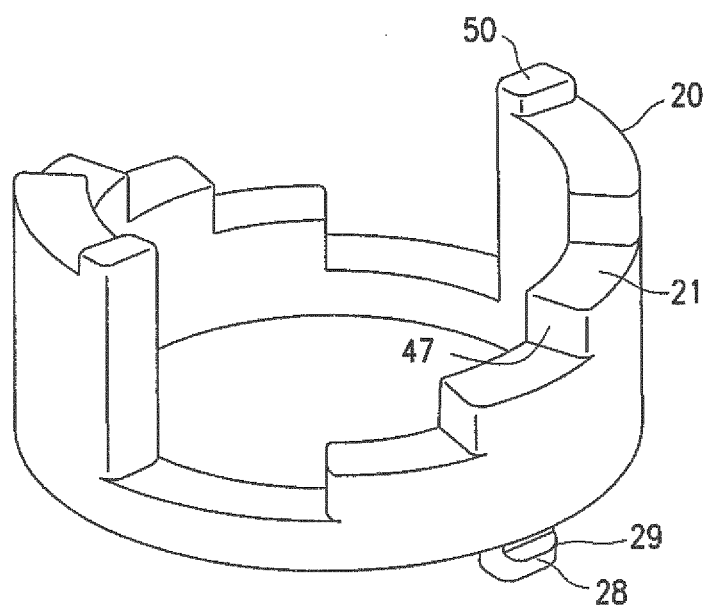
FIG. 6B is an enlarged perspective view of the staircase-like lower lock support shown in FIG. 3.

FIGS. 6A and 6B illustrate further details of the top endplate 13 and the lower lock support 20. The two sets of pistons 22 and upper lock supports 17 are joined by connecting members or struts 44. The pistons 22 have seal bosses 45 on which the seals 23 are mounted. The upper lock supports 17 have tiered lower support surfaces 18 and risers or alignment faces 46. The tiered or stepped support surfaces 18 of the upper lock supports 17 engage the stepped or tiered support surfaces 21 of the lower lock supports 20. The alignment faces 46 of the upper lock support are configured to engage the alignment faces 47 of the lower lock supports 20. The uppermost support surface of the lower lock support 20 has a lock support stop 50 which engages with the lower most alignment faces 46 of the upper lock support to prevent the lower lock support 20 from over rotating as it engages the upper lock support 17. The bottom of the lower lock support 20 also has the locking actuator transfer element 28 which engages the forward end 30 of the spring locking actuator 26 to transfer the actuation force from the locking actuator 26 to the lower lock support 20.

Figure 7:
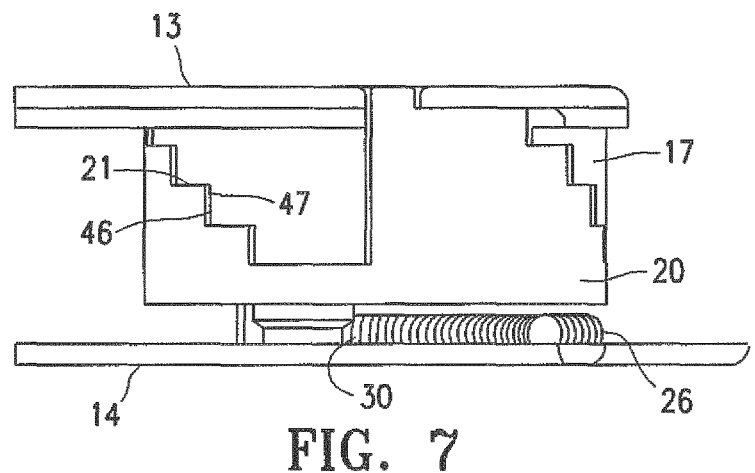
FIG. 7 is a partial side view of one of the locking mechanisms of the implant shown in FIG. 2.
Figure 8A:
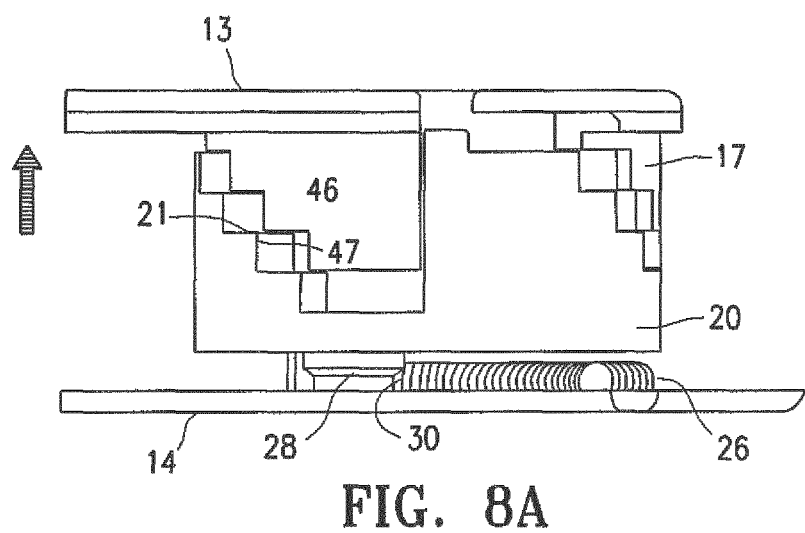
FIGS. 8A-9B are partial side views of the locking mechanism in FIG. 7 shown in different expanded and locked configurations.
Figure 8B:
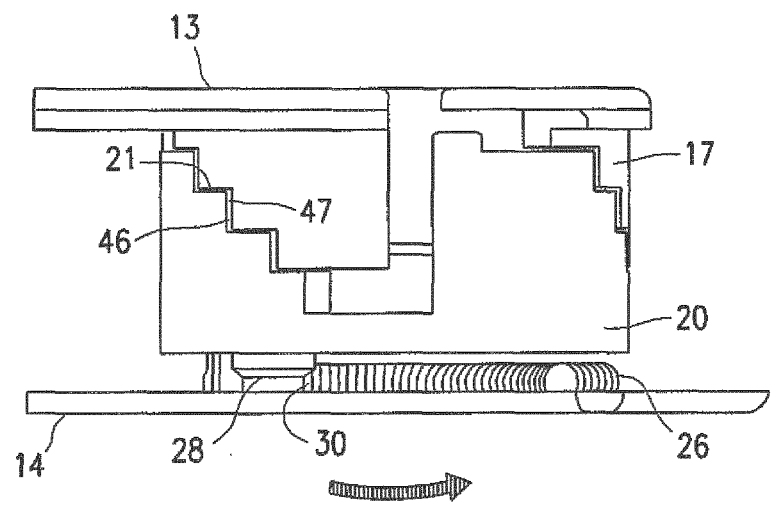
Figure 9A:
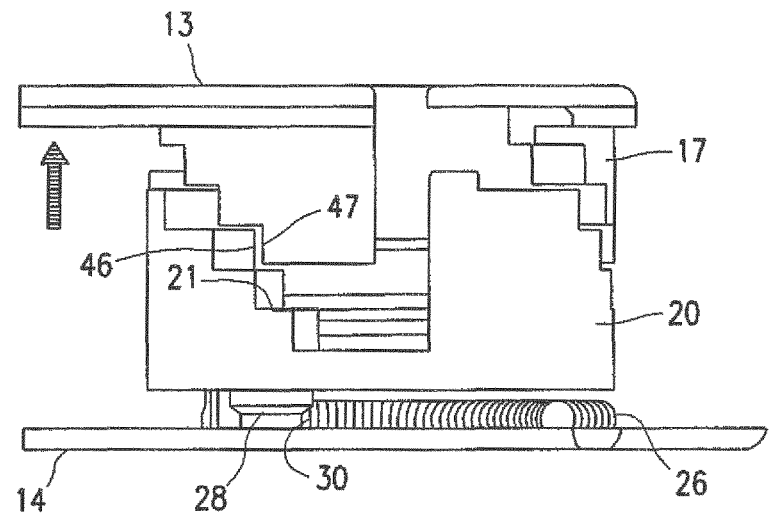
Figure 9B:
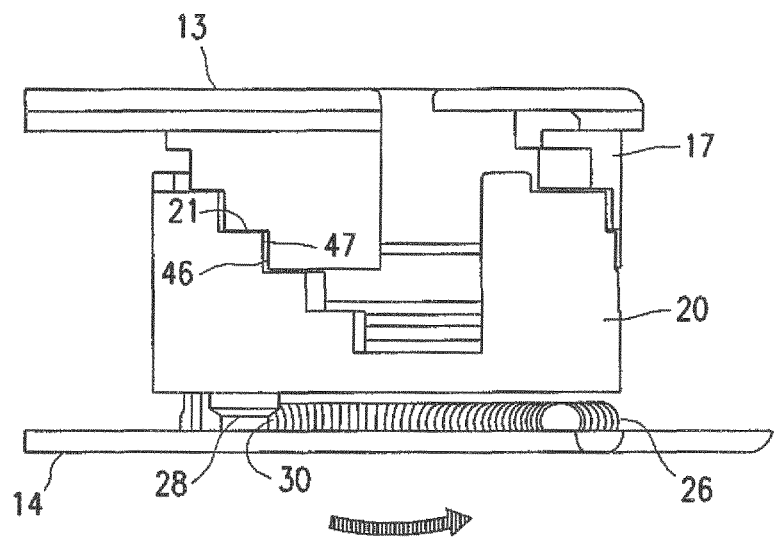
Figure 10A:
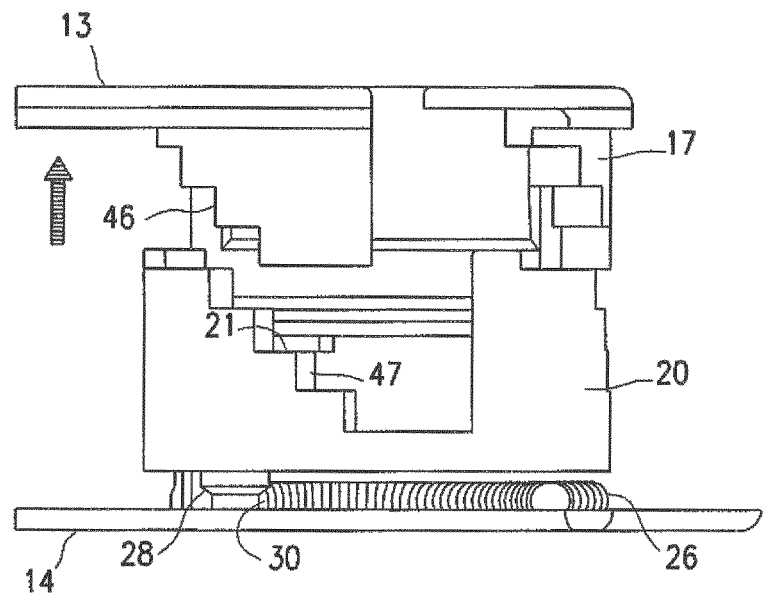
FIGS. 10A and 10B of the locking mechanism illustrate the expanded but unlocked configuration in FIG. 10A and the expanded and locked configuration in FIG. 10B.
Figure 10B:
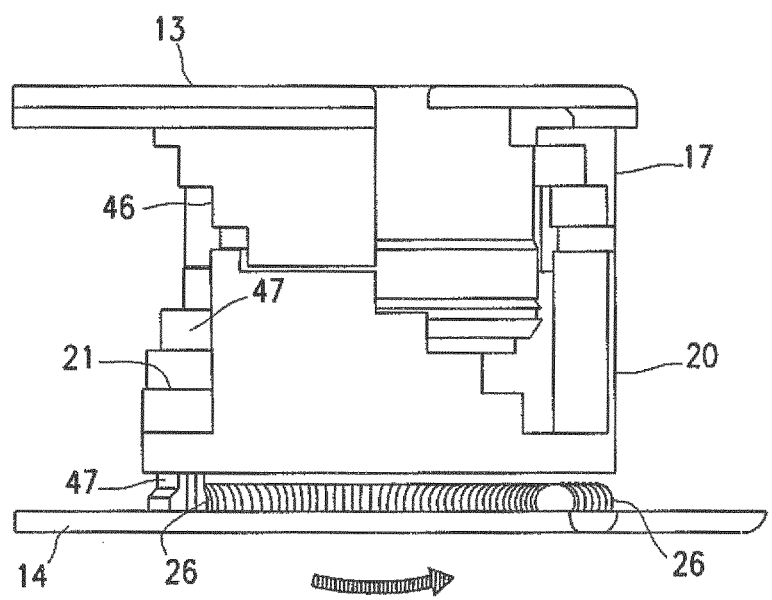

FIGS. 7 through 10B show details of the selectively expanding locking sequence of implant 10 with the housing 11 removed. The collapsed configuration is shown in FIG. 7 with the support surfaces 18 of the upper lock support 17 resting on the support surfaces 21 of the lower lock support 20. The locking actuator 26 is a biasing element, such as a spring, that engages the depending element or locking actuator transfer element 28 to urge the alignment faces of the lock supports in a direction where they contact. Thus, in one exemplary embodiment, the alignment faces 47 of the lower lock support 17 are forced against the alignment faces 46 of the upper lock support 17. The lock support stops 50 fit within the lower lock stop relief 52 (shown best in FIG. 6A) on the top endplate 13. When the cylinders 16 are pressurized, the pistons 22 raise the top endplate 13 and attached upper lock supports 17 (straight arrow) moving the support surfaces 18 of the upper lock support 17 off of the support surfaces 21 and moving the lower alignment faces 46 passed the upper alignment faces 47. When the alignment faces 46 of the upper lock support 17 have cleared the alignment faces 47 of the lower lock support 20, the locking actuators 26 (in this embodiment a compressed coiled spring) engaging the locking actuator transfer element 28 force the lower lock supports 20 to rotate (curved arrow in FIGS. 8B and 9B). The support surfaces 21 of the rotating lower lock supports 20 move to the next lower level of the support surfaces 18 of the raised upper lock supports 17 until the alignment faces 47 of the lower lock supports 20 engage the next level of the alignment faces 46 of the upper lock supports 17. The lower lock support 20 and upper lock support 17 then lock the top endplate 13 at this expanded level. This process repeats itself at each locking level (FIGS. 8A, 8B, 9A, 9B and 10A) until the top level (or somewhere between) is reached as shown in FIG. 10B. At this top level, the locking actuators 26 engage the locking actuator transfer elements 28 and the lower lock supports 20 are rotated so the lowermost alignment surface 46 of the upper lock support 17 engages lock support stop 50 of the uppermost support surface 21 of the lower lock support 20. At this highest locked level only the lowest support surfaces 18 of the upper lock supports 17 and the highest support surfaces 21 are engaged providing all of the locking support. As can be seen from FIGS. 10A and 10B the lowest support surfaces 18 of the upper lock supports 17 and the highest support surfaces 21 of the lower lock supports 20 can be wider than the other support faces to provide sufficient support material when only these two faces are engaged.

Figure 11A:
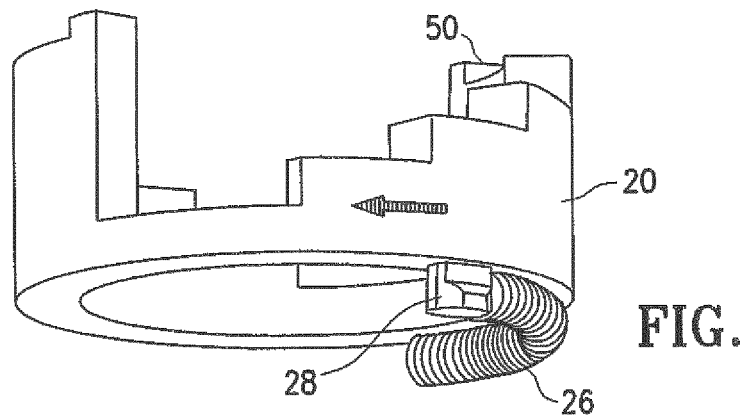
FIGS. 11A and 11B are perspective views of the lower lock support and spring locking actuator illustrating the operation thereof.
Figure 11B:
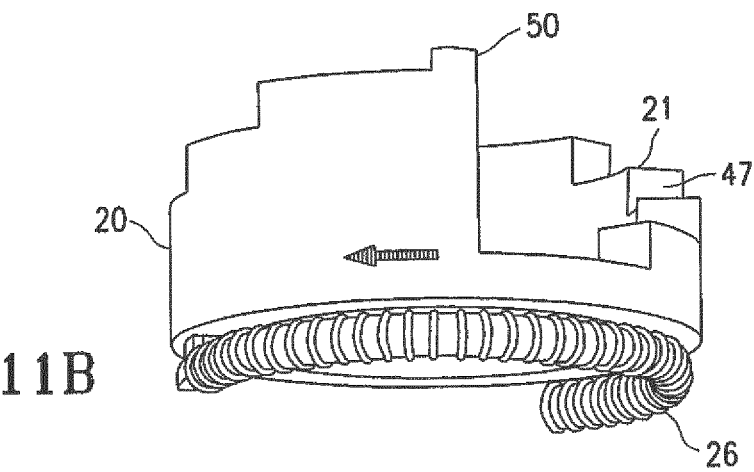

FIGS. 11A and 11B illustrate the operation of locking actuator 26. In this embodiment the spring locking actuator 26 is compressed into an arc beneath the lower lock support 20. One end of the spring locking actuator 26 is constrained by the housing 11 (not shown) and the other is engaged with the locking actuator transfer element 28. When the lower alignment faces 46 of the upper lock support 17 are raised above the upper alignment faces 47 of the lower lock support 20 by the extension of piston 22, the locking actuator 26 pushes against the locking actuator transfer element 28 and rotates the lower lock support 20 in a clockwise direction (arrow) as viewed from above. It should be noted that in the embodiment of the current implant as describe thus far, the angular orientation of the tiered upper and lower support surfaces 18 and 21 can vary when there is more than one set of supports. As shown in FIG. 3 the proximal lower support surfaces 21 are oriented clockwise as viewed from above and the distal lower support surfaces 21 are oriented counter-clockwise. This opposite orientation provides enhanced locking support for rotational forces applied to the implant.

Figure 11C:
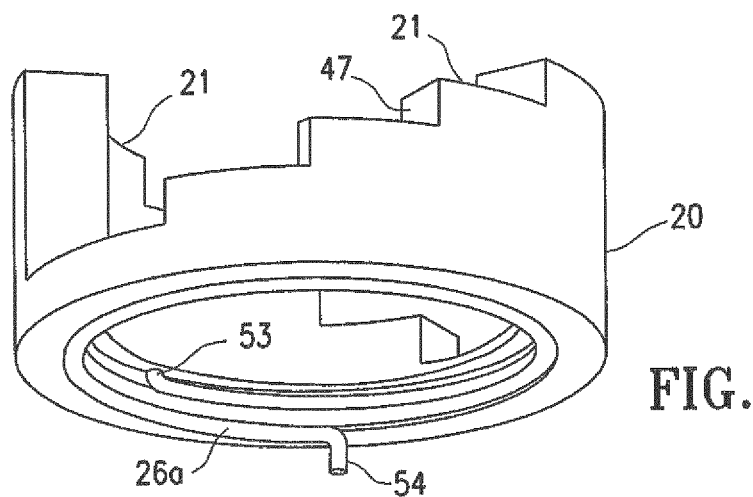
FIG. 11C is a perspective view of an alternate locking mechanism and locking actuator embodying features of the invention.

An alternate locking actuator 26a is shown in FIG. 11C as a torsion spring. This locking actuator 26a has constraining tab 53 secured to the lower lock support 20 and constraining tab 54 secured to the housing 11a. Just as the compression spring shown in FIGS. 11A and 11B applies a force to the lower lock support 20a to rotate it, the torsion spring in FIG. 11C does the same. An extension spring would work equally as well as a locking actuator 26a. Spring actuators can be made of an appropriate biocompatible material such as stainless steel, NITINOL, titanium or a suitable polymer. Locking actuators are not limited to springs. A wide variety of mechanisms can be used to actuate the lower lock supports 20, including but not limited to, a linear drive, an externally actuated tensile member, a worm gear, an inflated member such as a balloon or bellows, a magnet, a rotational drive such as a micro motor, a super elastic shape memory element, and the like.

Figure 12A:
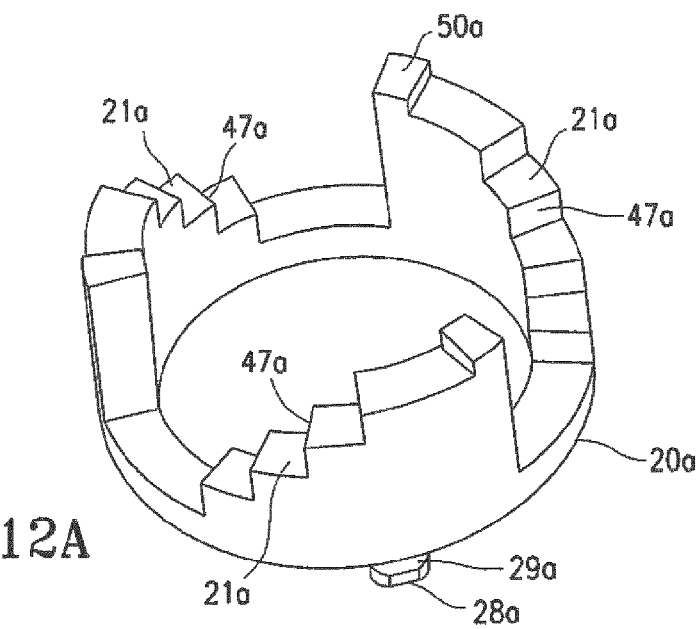
FIGS. 12A-12C are perspective views of alternate lower lock support designs embodying features of the invention.
Figure 12B:
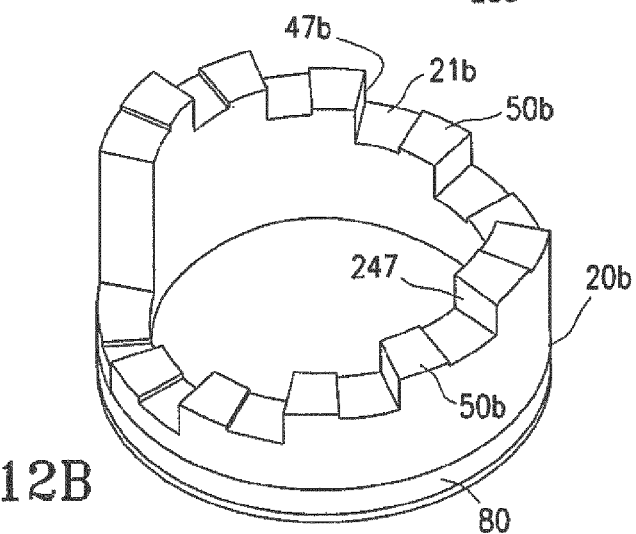
Figure 12C:
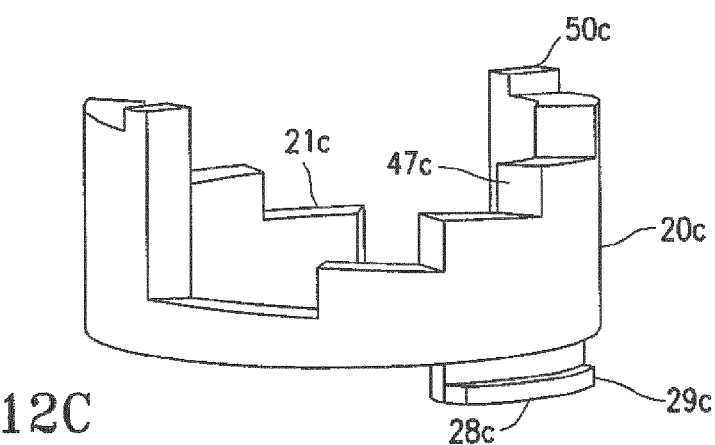

FIG. 12A through 12C show variations of the lower lock support 20 described above. In FIG. 12A a tri-set lock support 20a is shown whereby there is are three sets of upper support surfaces 21a, upper alignment surfaces 47a and lock support stops 50 rather than the 2 sets described above. This tri-set lower lock support 20a has two advantages over the 2 sets design, 1) there are three support columns rather than two locking the implant 10 in an expanded state thereby creating a more stable lock and 2) the tri-set lower lock support—20a has to move or rotate much less for each locking level. This last advantage is significant when the locking actuator is a spring such as spring locking actuator 26 as this places less strain on the spring to achieve the required locking force at each step. Each lower lock support column will have a corresponding upper lock support column (not shown). The upper support surfaces 21 and lower support surfaces 18 are not limited to 2 or 3 sets of surfaces. Any number of sets of support surfaces including a single set may be employed.

FIG. 12B shows an inter-digitating lower lock support 20b. Each of the inter-digitating upper support surfaces 21b on the inter-digitating lock support 20b is paired with an inter-digitating stop 50b which when paired with matching inter-digitating support surfaces and stops of an upper lock support (not shown) prevents the inter-digitating support surfaces 21b from moving relative to the inter-digitating support surfaces of an upper lock support to unlock the implant 10b without the inter-digitating lower support faces first lifting above the inter-digitating stop 50b. This design provides an enhanced locking feature.

Generally the lower support surfaces 18 and the upper support surfaces 21 are horizontal to maximize vertical support in the locked implant. However, the locking support 20c shown in FIG. 12C provides an enhanced locking feature by providing inclined support surfaces 21c which have a slope relative to the horizontal which requires matching inclined lower support surfaces on the upper lock supports (not shown) to be lifted above the inclined upper support surfaces 21c before the upper lock support can be rotated to unlock the implant 10c.

FIGS. 12A and 12C show various lengths of locking actuator transfer elements or depending elements 28. The locking actuator transfer element 28 can vary in length depending on how much engagement is desired between the locking actuator transfer element 28 and the locking actuator slots 27. The locking actuator transfer element 28 includes one or more transfer element tabs 29a and 29c which vertically constrain the lower lock support 20 to the locking actuator slots 27 in the housing 11. The wider locking actuator opening 42 described above enables insertion of the locking actuator transfer element 28 with transfer element tabs 29a and 29c into the locking actuator slots 27 in housing base 12 at the rotational position where the locking actuator transfer element 28 is aligned with the locking actuator opening 42. In other rotational positions the transfer element tabs are constrained by lateral extensions 49 (shown in FIG. 4B) on the sides of the narrower locking actuator slots 27. In this manner the locking actuator transfer element 28 provides both the function of transferring force from the locking actuator 26 to the lower lock support 20 as well as constraining the lower lock support 20 to the housing 11. This later function prevents the frictional forces between the lower alignment faces 46 and the upper alignment faces 47 created by the biased spring locking actuator 26 from lifting the lower lock support 20 along with the upper lock support 17 when the upper lock support 17 is lifted by the piston 22.

As an alternative to the locking actuator transfer element 28, the embodiment shown in FIG. 12B depicts a locking actuator guide channel 80. This locking actuator guide channel 80 engages a tensile member (not shown) which transfers actuation force from the locking actuator 26 to the lower lock support 20. Tensile members can be an of a number of known elements such as sutures made of polymers or natural materials, metal cable, plastic or metal rod and the like.

Figure 13A:
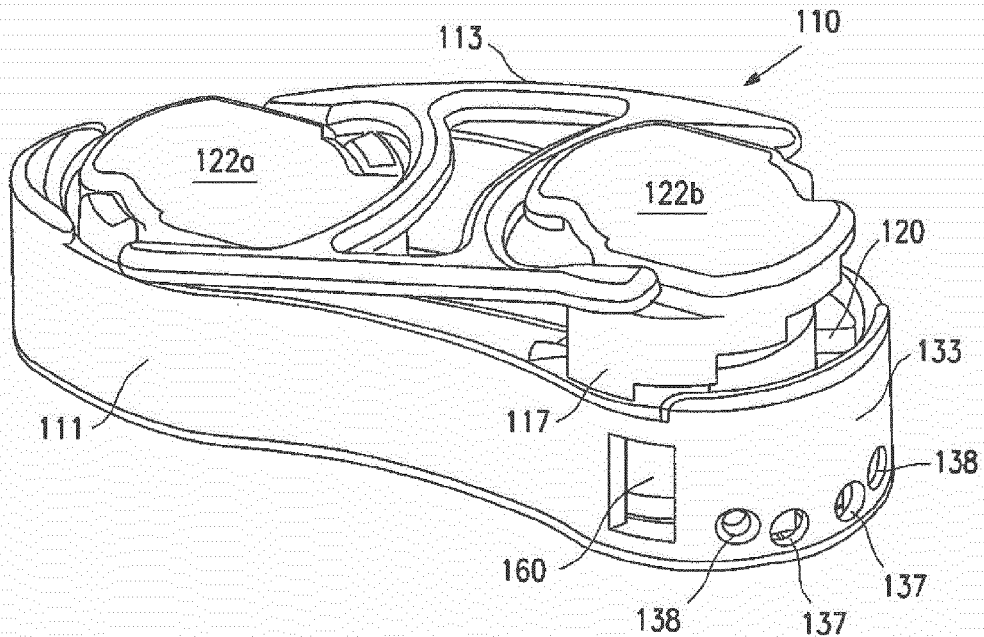
FIGS. 13A-13B are perspective and side views respectively of an alternative implant embodying features of the invention which has an articulating top end plate.
Figure 13B:
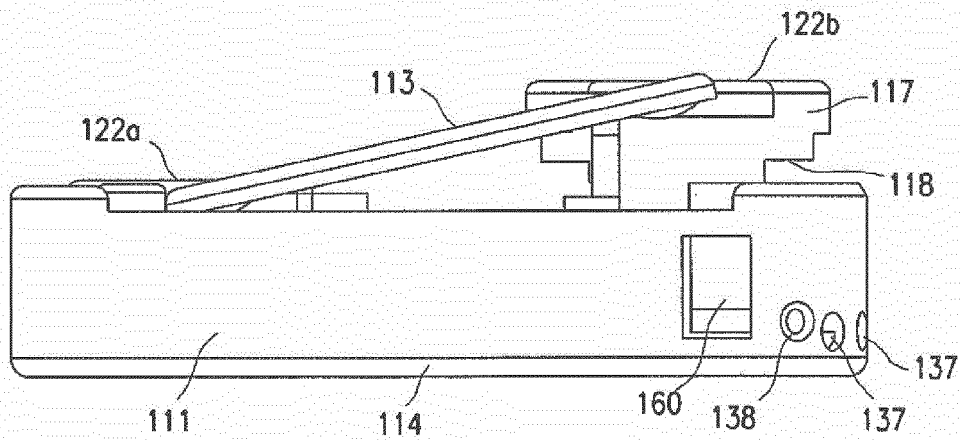

FIGS. 13A and 13B illustrate an alternate design of an implant 110 embodying features of the invention. The implant 110 has independent actuation of the distal piston 122a and proximal piston 122b. The two pistons 122a and 122b are interconnected by an articulating top endplate 113 which allows independent lift and locking of each side of the implant 110. This independent lift and locking of both ends of the implant 110 enables the implant to conform to intervertebral endplates that have uneven lateral heights between them. Further, this independent lift and locking allows the implant 110 to be used to create varying lateral heights between vertebral endplates which can be useful to compensate for a scoliosis in the spine.

Implant 110 has a housing 111 which has an alternate delivery tool anchor 160 located in it as well as alternate pressure input ports 137. A variety of anchor design or pressure ports can be used with any of the embodiments of the current device without departing from the scope of this invention. Lock and unlock access ports 138 are also located on this housing 111. These ports are used to guide lock and unlock mechanisms (not shown) which can be manipulated externally to the implant 110 to actuate the lower lock support 120 to not only move it under the upper lock support 117 to hold the piston 122b and articulating endplate 113 in an expanded position, but also to move the lower lock support 120 away from the upper lock support 117 to allow the piston 122b and articulating endplate 113 to collapse back into the housing 110. This later action maybe desirable to remove the implant 110 from or reposition the implant within the intervertebral space. A variety of lock/unlock mechanism can be used with the current invention such as but not limited by, a tensile member including suture thread and metallic cable, a compressive member such as a metallic or polymer rod, pressurized fluid, a rotating drive, a super elastic shape memory element, and the like.

Figure 14A:
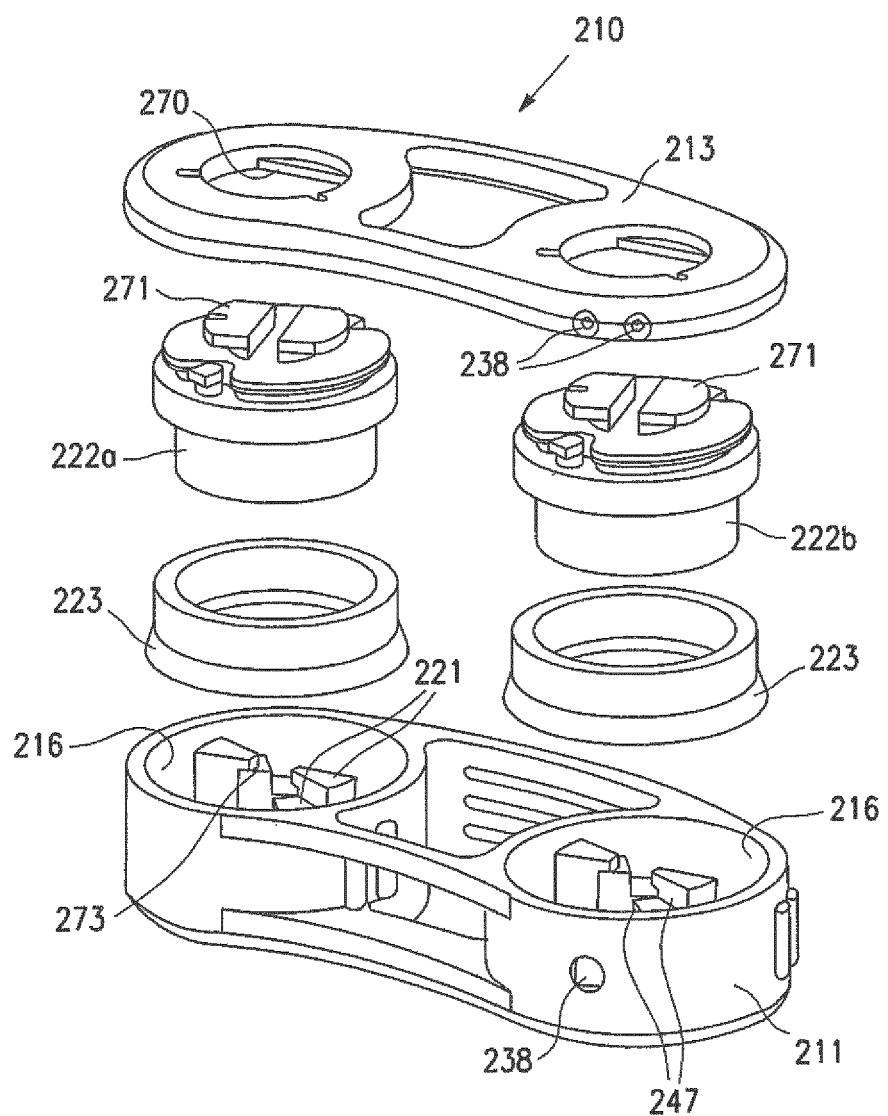
FIG. 14A is an exploded perspective view of yet another alternative implant embodying features of the invention which has the lower lock supports within the extendable pistons.
Figure 14B:
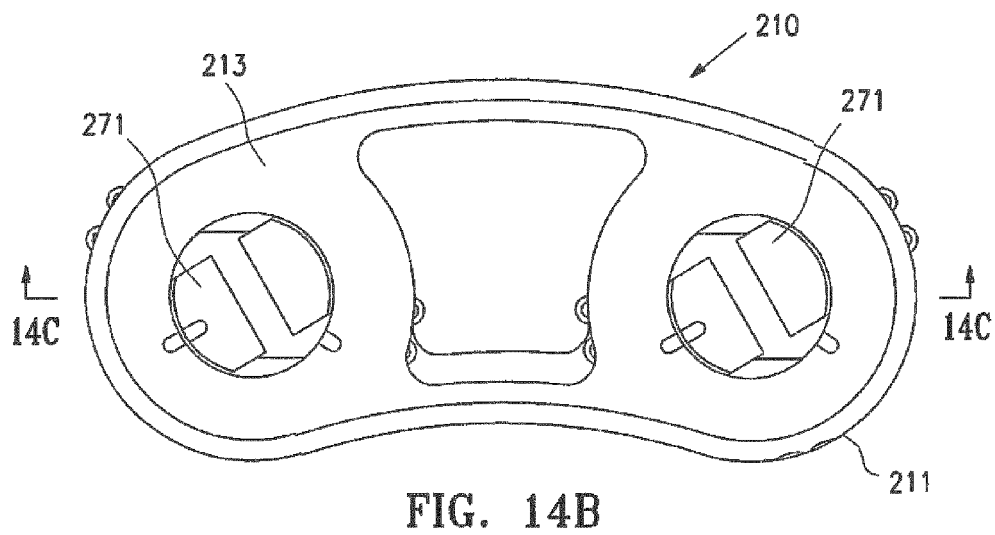
FIG. 14B is a top view of the implant shown in FIG. 14A.
Figure 14C:
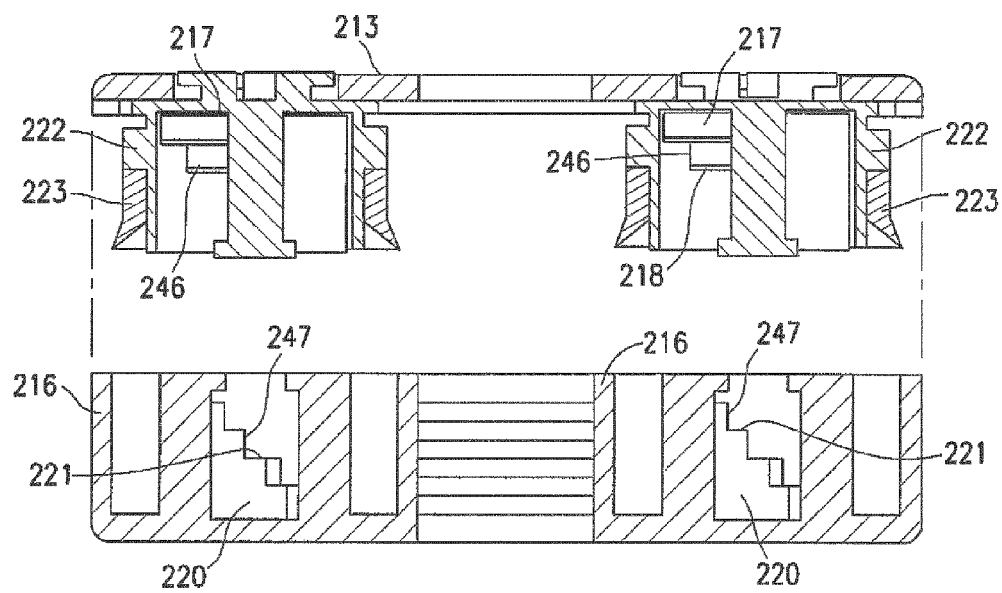
FIG. 14C is a side cross-sectional view through line 13C-13C of the implant shown in FIG. 14B.

FIGS. 14A-14C depict yet another alternate implant 210 that embodies features of the invention. Implant 210 has an interfacing top plate 213 which connects to separate and freely rotating pistons 222 via the piston capture plate 270 on the interfacing top plate 213 and the piston heads 318 on the rotating pistons 222ab. The rotating pistons 222ab also interiorly contain upper lock supports 217 with support faces 218 and alignment faces 246. Seals 223 are mounted on the rotating pistons 222ab and the seals 223 and rotating pistons 222ab fit into internal cylinders 216 that are located on the housing 211. The internal cylinders 216 have lower lock supports 220 with support surfaces 221 and alignment faces 247 as well as lower retaining features 273. The housing 211 also contains one or more pressure input ports 238.

In use, the implant 210 is inserted into the intervertebral body space in a collapsed state and fluid pressure is delivered through the pressure input port(s) 238 to the internal cylinder (s) 216 to raise the seal(s) 223 and rotating piston(s) 222ab out of the internal cylinder(s) thereby raising the interfacing top plate 213 and expanding the implant 210. Once the rotating pistons 222*ab* have been raised such that the lower alignment faces 246 of the upper lock supports 217 have cleared the upper alignment surfaces 247 of lower lock supports 220, an actuator (not shown) rotates the rotating pistons 222*ab* such that the lower support surfaces 218 of the upper lock supports 217 are moved above the upper support surfaces 221 of the lower lock supports 220, to thereby lock the implant 210 in the expanded configuration. The actuator can be one or more tensile members such as suture threads or cables that extend from the user into the implant 210 through the lock and unlock access ports 238 on the interfacing top plate 213 to the piston head 271. Applying tension to one or more tensile members when the piston is in an extended configuration will rotate the piston heads 271 such that the support surfaces 218 of upper lock supports 217 are moved above the support surfaces 221 of the lower lock supports 220 thereby locking the implant 210. Alternately or in addition to applying tension to lock the implant 210 in an expanded configuration, apply tension to one or more tensile members will rotate the piston heads 271 such that the lower support surfaces 218 are moved away from the upper support surfaces 221 thereby unlocking the implant 210 and allowing the rotating pistons 22*ab*2 to seat back into the internal cylinders 216 such that the implant 210 is once again in a collapsed configuration.

Figure 15:
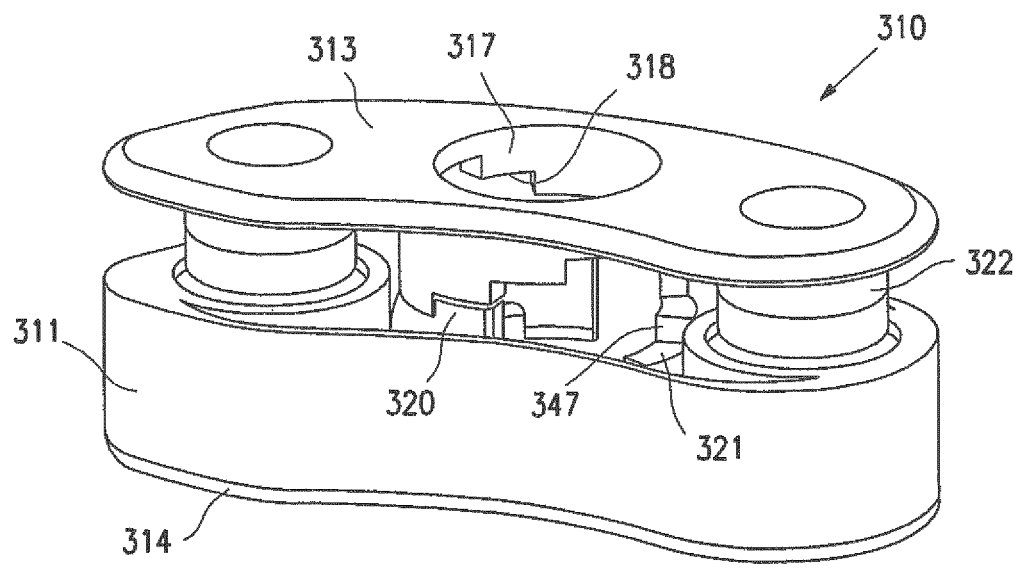
FIG. 15 is a perspective view of an alternate implant design having features of the invention wherein the locking mechanism surrounds a central opening in the top end plate.

FIG. 15 illustrates an alternate implant design 310 embodying features of the invention which has a housing 311, top end plate 313 and pistons 322 similar to the prior embodiments. This implant 310 has upper lock supports 317 and lower lock supports 320 within a central portion of the implant. The upper lock supports 317 are secured to the top end plate 313 and the lower lock supports 320 are secured to the base 314 with depending elements (not shown) as was described above and are moved as in the prior embodiments.

Figure 16:
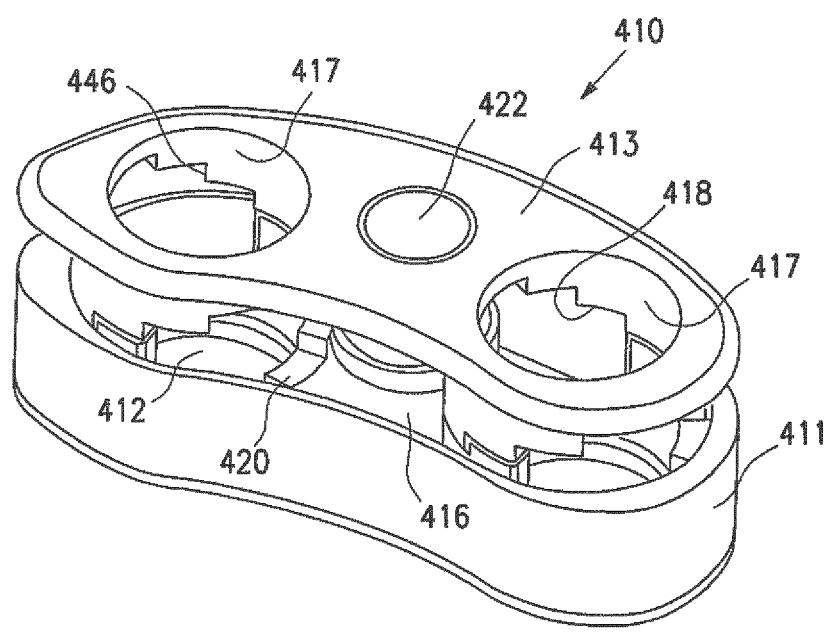
FIG. 16 is a perspective view of an alternate implant design having features of the invention wherein the expanding piston is centrally located and locking mechanisms are provided on both sides of the expanding piston.

FIG. 16 illustrates an alternate implant design 410 embodying features of the invention which has a housing 411, top end plate 413 and a centrally located piston 422 similar to the prior embodiments. This implant 410 has upper lock supports 417 and lower lock supports 420 distal and proximal to the centrally located cylinder 416 and piston 422. The upper lock supports 417 are secured to the top end plate 413 and the lower lock supports 420 are secured to the base 412 and are moved as in the prior embodiments via depending elements (not shown) as was described above.

Figure 17:
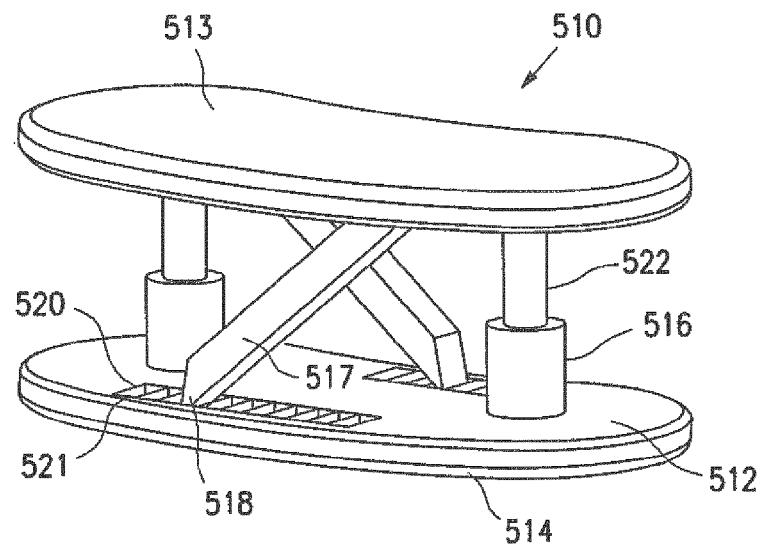
FIG. 17 is a simplified schematic illustration of an alternate implant design having ratchet and pawl locking members between the top and bottom plates of the implant.

FIG. 17 shows another alternate implant 510 which has a pair of pistons 522 and which has a locking support system which includes ratchets 520 on the base 512 and pawls 517 pivotally mounted to and depending from the top end plate 513. Expansion of the pistons 522 causes the free ends 518 of pawls 517 to engage recesses 520 in the ratchets 521 so as to lock the top end plate 513 in an extended configuration.

Figure 18:
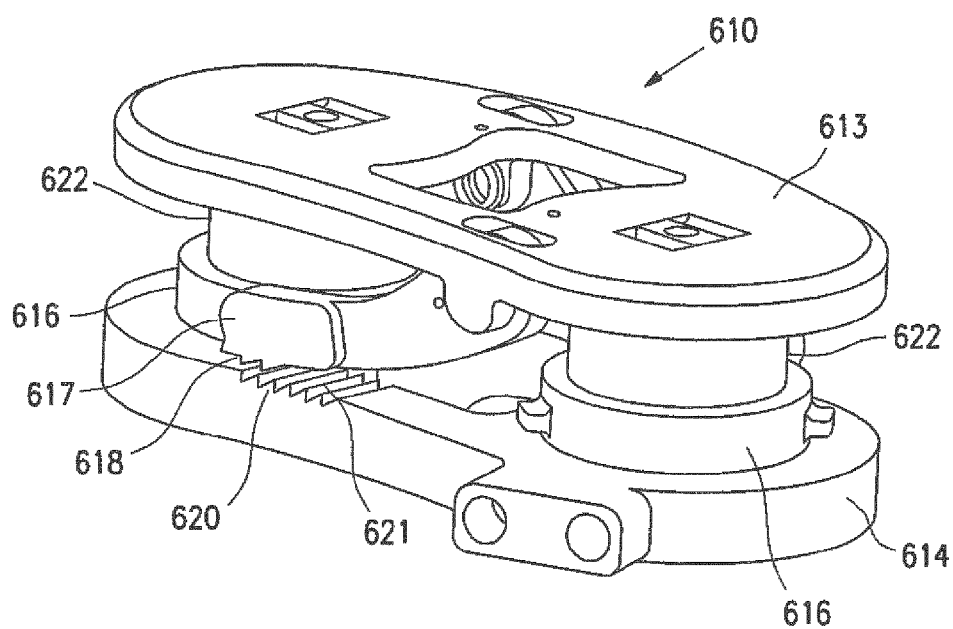
FIG. 18 is a perspective view of an alternative implant design with ratchet and pawl locking members between the top and bottom plates of the implant.

FIG. 18 illustrates another alternative implant design 610 which is similar to that shown in FIG. 17. In this embodiment the free end of the pawl 617 has a plurality of teeth 618 to provide greater effective contact between the pawl 617 and the ratchet 621 for locking of the implant 610.

Figure 19:
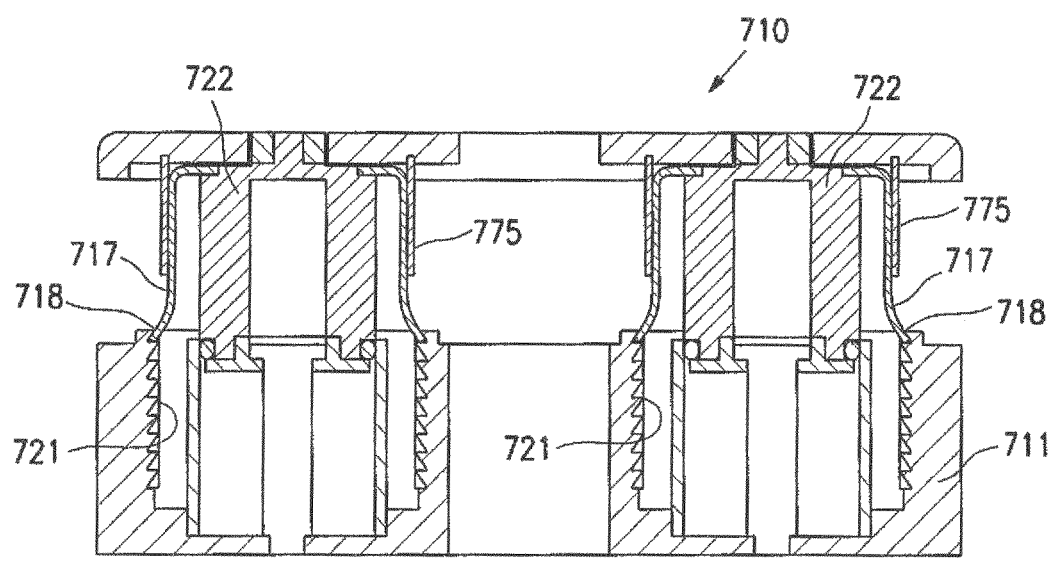
FIG. 19 is a cross sectional perspective view of an implant design with ratchet and cantilevered spring members between the top and bottom plates of the implant.

FIG. 19 is the cross section of another embodiment of implant 710 embodying features of the invention. In this embodiment the pistons 722 are surrounded by upper lock support 717 which has at least one cantilever extension ending at the support surface 718. The support surfaces 718 are captured by the recessed support surfaces 721 which are located on the inner wall of the housing 711. Once the pistons 722 are expanded in an upward direction, the support surfaces 718 of the upper lock support 717 engages the recessed support faces 721 locking the implant 710 in place. The upper lock support 717 can be rotated relative to the piston 722 and housing 711 to disengage the support surfaces 718 from the support faces 721 to unlock the implant 710 and lower the pistons 722 as needed. Alternately the implant 710 can be unlocked by rotating the upper lock support constraints 775 relative to the upper lock support 717 to press on the cantilever extensions and disengage the support surfaces 718 from the support surfaces 721.

FIGS. 20A-31 illustrate a variety of suitable means for locking extendable members such as pistons in extended configurations. FIGS. 20A, 20B, 21A, 21B, and 22-31 show variations of lower lock supports and upper lock supports. In each of these variations there are support surfaces on the lower lock supports which engage support surfaces on the upper lock supports.

Figure 20A:
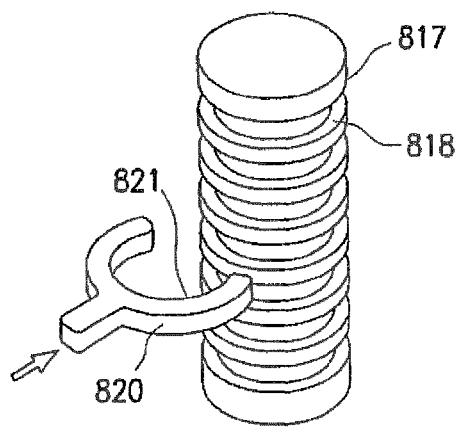
FIGS. 20-29 schematically illustrate various means for locking an expanding member of implants in extended configurations embodying features of the invention.
Figure 20B:
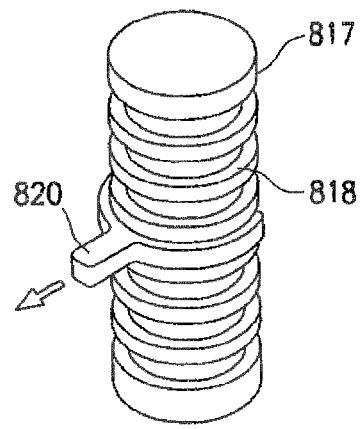

In FIGS. 20A and 20B support surfaces 818 comprise grooves set into the upper lock support 817. The lower lock support 820 is a U-shaped tong which is configured to advance (as indicated by the arrow in FIG. 20A) towards the upper lock support 817 and to engage one of the grooves with its upper support surface 821 for locking an implant not shown in these drawings. Lower lock support 820 is withdrawn (as indicated by the arrow in FIG. 20B) from the groove to disengage the lower lock support and unlock the implant.

Figure 21A:
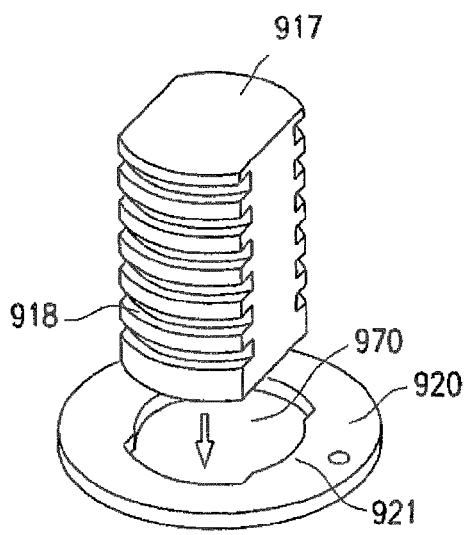
Figure 21B:
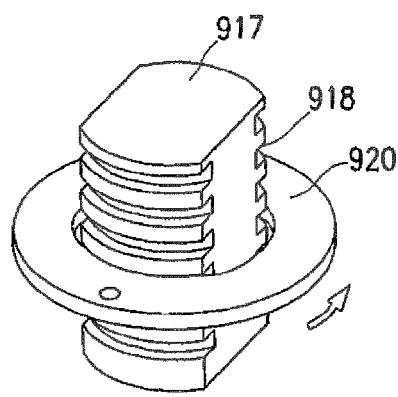

In the variation shown in FIG. 21A, the lower lock support 920 is a plate with an upper lock clearance opening 970 that is shaped to allow passage of the cylindrical flat sided upper lock support 917 through the lower lock support 920 (arrow). As shown in FIG. 21B, once the lower lock support 920 is positioned at the desired location it can be rotated approximately 90° (arrow) to engage the support faces of the lower lock support 920 with the support surfaces 918 of the upper lock support 917. The shape of the upper lock support 917 and mating upper lock clearance opening 970 on the lower lock support 920 are not restricted to the profile shown in FIGS. 21A and 21B nor is the locking actuation restricted to 90° rotation of one of the elements but can vary to any number of shapes that allow passage in one configuration but constraint when one of the elements is moved to another configuration.

Figure 22:
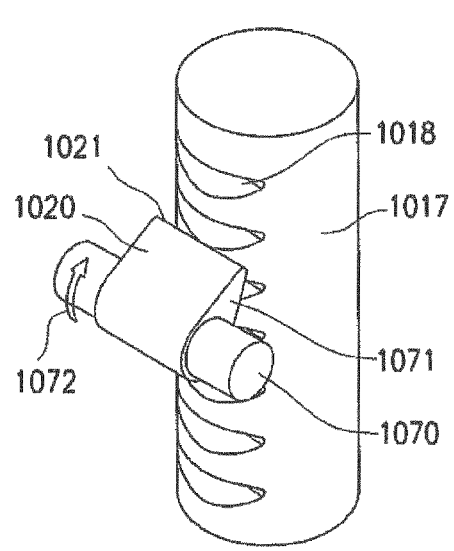

In FIG. 22, the upper lock support 1017 is a cylinder with notches cut to create support surfaces 1018. The lower lock support 1020 is a pivoting pin 1070 with a pawl 1071 for the lower support surface 1021. In the configuration shown, the support surface is biased as indicated by the arrow 1072 to allow the upper lock support 1017 to rise with an expandable member of an implant and to prevent the upper lock support from dropping. This allows the device to lock at each level when the subsequent support surface 1018 of the upper lock support 1017 engages the support surface 1021 of the lower lock support 1020. In this variation having features of the present invention, the upper lock support 1017 can also be lowered by moving the pivoting pin 1070 of the lower lock support 1020 away from the upper lock support 1017 to disengage the support surface 1021 from the support surface 1018.

Figure 23:
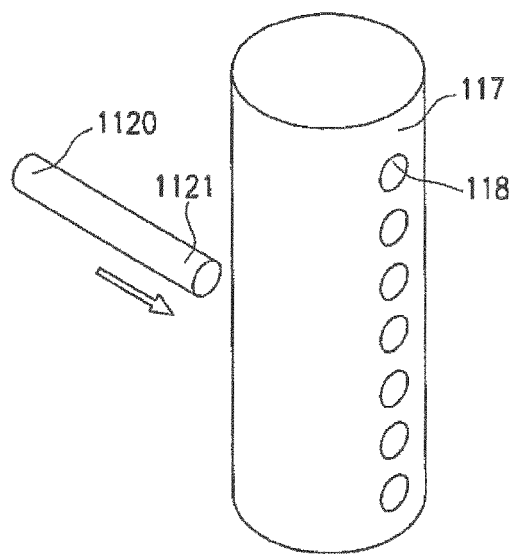

FIG. 23 shows yet another embodiment having features of the invention where the lower lock support 1120 is a pin configured to engage (arrow) support surfaces 1118 located in the upper lock support 1117. The lower lock support 1120 does not have to engage the full thickness of the upper lock support 1117 as shown in this figure, nor does the support surface 1118 have to extend through the entire thickness of the upper lock support 1117 but rather can engage any portion of the upper lock support 1117 that is sufficient to lock an implant in position. This embodiment also allows a variety of shapes of pins 1120 and matching support surfaces 1118.

Figure 24:
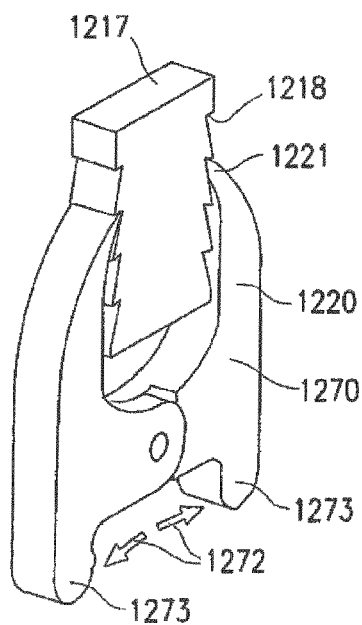

In FIG. 24 the lower lock support 1220 is a grip with two pivoting jaws 1270, the ends of which have support surfaces

1221. The upper lock support 1217 has a series of notches 1271 which have the support surfaces 1218. A lock actuator such as a compressive spring (not shown) can apply force (as shown by the arrows 1272) to the grip base extensions 1273 to lock the device. This variation having features of the invention allows the upper lock support 1217 to move upwards but prevents downward motion thereof. Downward motion of the upper lock support 1217 can be allowed by reversing the force on grip base extensions 1273.

Not all locking systems embodying features of the invention require the engagement of support surfaces of the upper lock supports directly on top of the support surfaces of the lower lock supports. A frictional support can be created to lock the device as shown in FIGS. 25 through 32.

Figure 25:
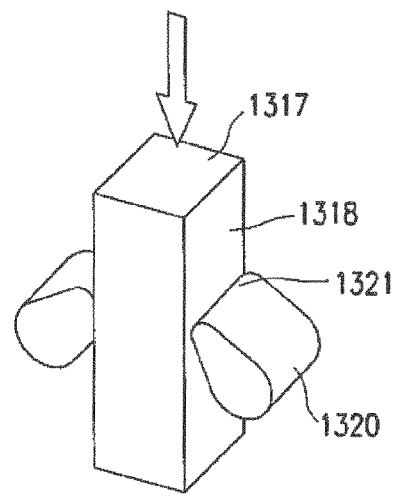

In FIG. 25 the upper lock support 1317 has one or more flat faces as the support surfaces 1318. The lower lock support 1320 has one or more pivoting pawls that have a support surface 1321 that engage the support surface 1318 and supports a load (arrow).

Figure 26:
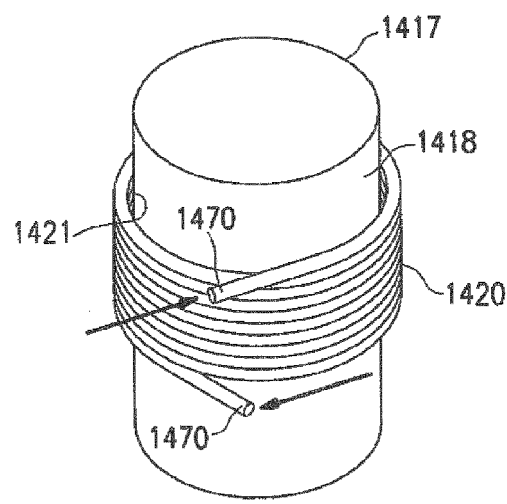

In FIG. 26 the upper lock support 1417 has an exterior support face 1418 which is gripped by the support face 1421 on the inner diameter of the wrapped lower lock support 1420. This lower lock support 1420 can be a torsion spring that in its free state grips the upper lock support 1417 and releases the upper lock support when a force (arrows) is applied to one or more of its ends 1470 as shown to increase the spring's inner diameter. The reverse is possible where in its free state the lower lock support 1420 allows movement of the upper lock support 1417 inside the inner diameter. When a tensile force is applied to the ends 1470 to reduce the inner diameter, the lower lock support grips the support surface 1418 of the upper lock support 1417 to lock the implant.

Figure 27A:
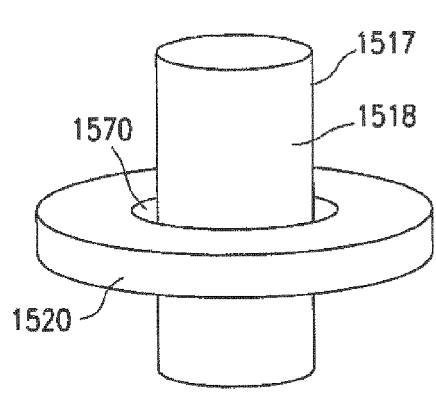
Figure 27B:
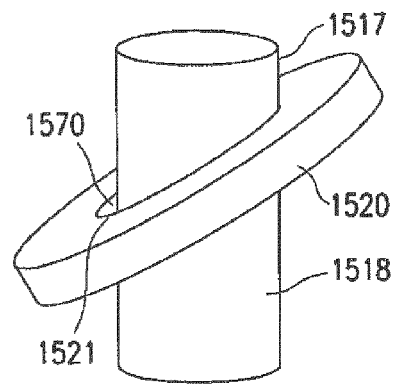

FIGS. 27A and 27B show another variation which can be described as a canted washer type device. The lower lock support 1520 is a plate with an upper lock clearance opening 1570 which allows relative movement of the upper lock support 1517 as shown in FIG. 27A. When the lower lock support 1520 is canted as shown in FIG. 28B the edge of the upper lock clearance opening 1570 comprises a lower support surface 1521 which engages the upper support surface 1518 which is the outer surface of the upper lock support 1517 locking it relative to the lower lock support 1520.

Figure 28:
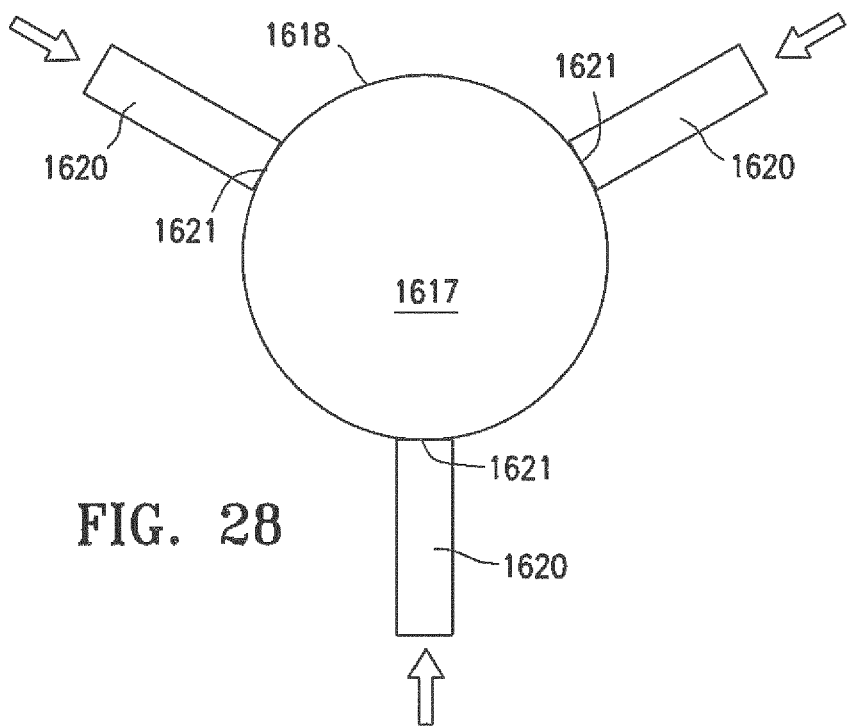

Yet another variation of the gripping lock of the current invention is shown in FIG. 28. In this variation the lower lock support 1620 comprises of one or more jaws which have support surfaces 1621 that are configure to be forced against the support surface 1618 of the upper lock support 1617 to produce friction to lock the device in place.

Figure 29:
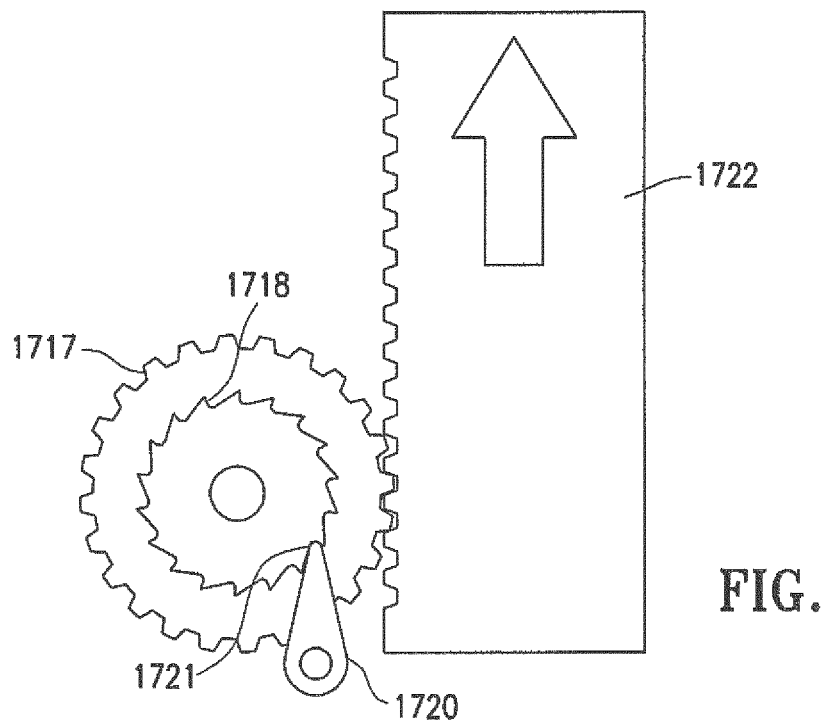

FIG. 29 illustrates a lower lock support 1720 which comprises a pivot and pawl as has been detailed above. The end of the pawl comprises a lower support surface 1721 which engages an upper support surface 1718 on the upper lock support 1717. In this embodiment the upper lock support 1717 is rotated counter clockwise by an expanding element (not shown). This rotation in turn raises the piston 1722 which expands the implant. In this manner the upper lock support 1817 is integrated into the lifting mechanism to engage the lower lock support 1720 and lock the implant as it expands.

Figure 30:
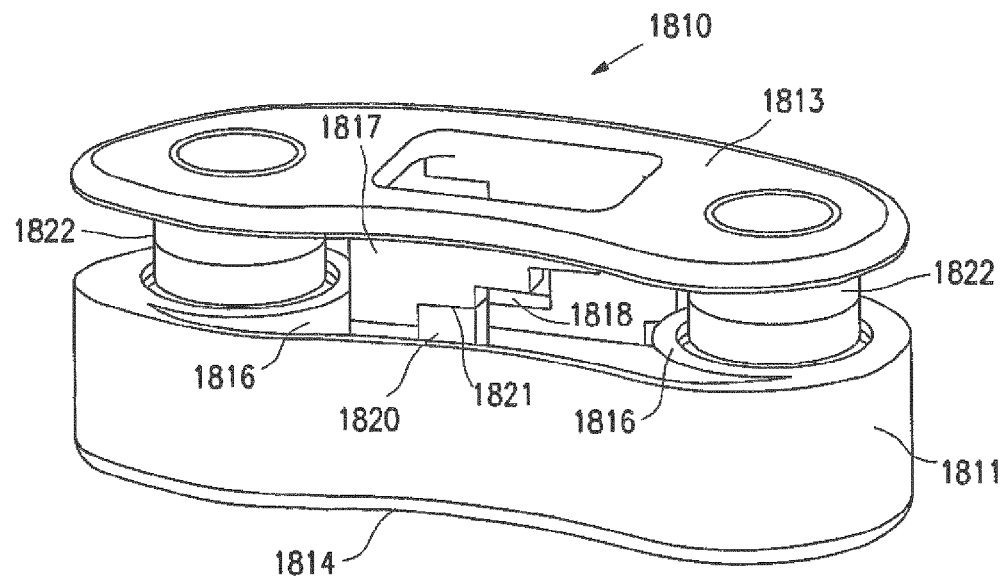
FIG. 30 is a perspective view of yet another alternate implant design having features of the invention wherein the locking mechanism has straight upper and lower interfitting lock supports.

FIG. 30 illustrates yet another alternative implant 1810, similar to that shown in FIG. 1 except that the upper locking member 1817 and lower locking member 1818 have a linear shape rather than the arcuate shape of the prior embodiments. The implant 1810 generally has a housing 1811, a top plate 1813, a bottom plate 1814, pistons 1822 and cylinders 1816. The upper locking member 1817 has support surfaces 1818 and the lower locking member 1820 has support surfaces 1821. The implant 1810 has a locking actuator (not shown).

FIGS. 31A-31G illustrates another implant 1910 embodying features of the invention which has upper locking members 1917 with grooves 1970 having support surfaces 1918 and lower locking member 1920 with locking surfaces 1921. The lower locking member 1920 is a wire-form which encircles the exterior of both upper locking members 1917 and is configured to seat within the grooves 1970. Expansion of the lower locking member 1920 (arrows in FIG. 31B) by the locking actuator (not shown) causes the lower locking member 1920 to be pulled out of the groove 1970 and allows the upper locking member 1917 to rise with the expansion of the implant. Release of this expansion of the lower locking member 1920 (arrows in FIG. 31A) allows the lower locking member 1920 to seat back into the groove 1970 locking the implant 1910.

Figures 31A, 31B:
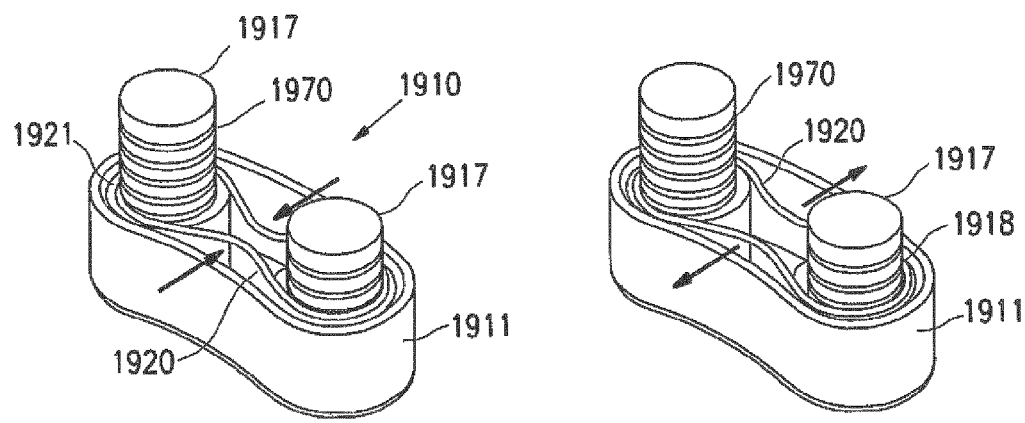
FIG. 31A-31G illustrate an alternative implant locking mechanism in which a wire-form surrounds a pair of upper support members with grooves configured to receive the wire-form.
Figure 31C:
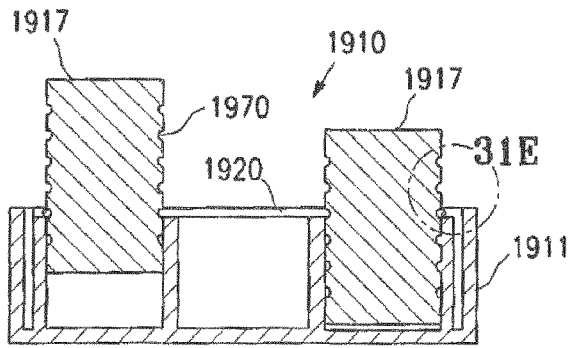
Figure 31E:
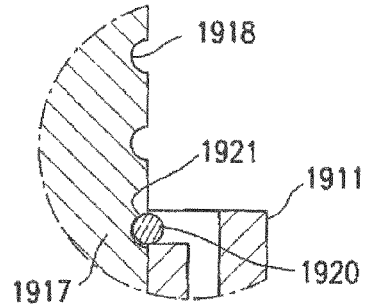
Figure 31D:
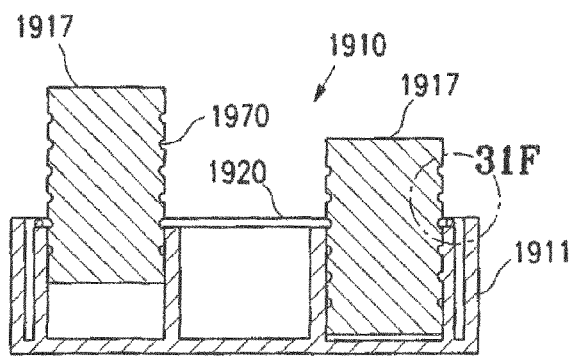
Figure 31F:
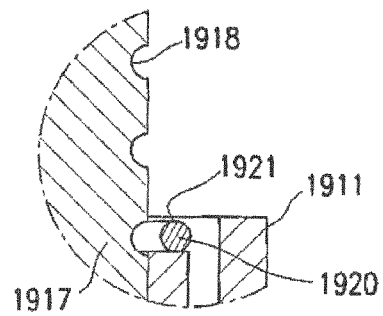
Figure 31G:
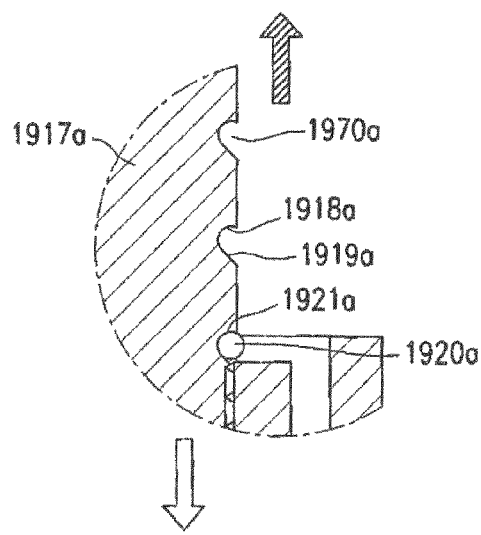

FIG. 31G illustrates a detail of an alternate implant 1910*a* embodying features of the invention which has upper locking members 1917*a* with grooves 1970*a* having support surfaces 1918*a* and lower locking member 1920*a* with locking surfaces 1921*a*. The lower locking member 1920*a* is a wire-form which encircles the exterior of both upper locking members 1917*a* and is configured to seat within the grooves 1970*a*. The support surface 1918*a* locks on the supports surface 1921*a* when there is a compressive or downward force (hollow arrow) on the upper locking member 1917*a* locking the implant 1910*a*. Upward force or extension (solid arrow) of the upper locking member 1917*a* causes the lower locking member 1920*a* to ride on the disengaging surface 1919*a* and out of the groove 1970*a* allowing the upper locking member 1917*a* to rise with the expansion of the implant 1910*a*.

Figure 32A:
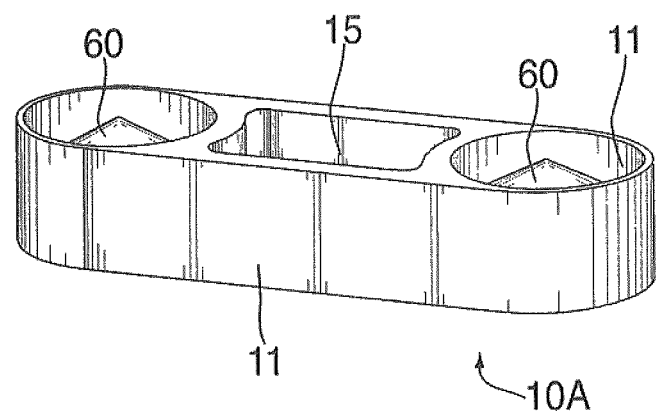
FIGS. 32A and 32B are perspective views of a further alternative embodiment of the present invention including locking, conical bone engaging anchors.
Figure 32B:
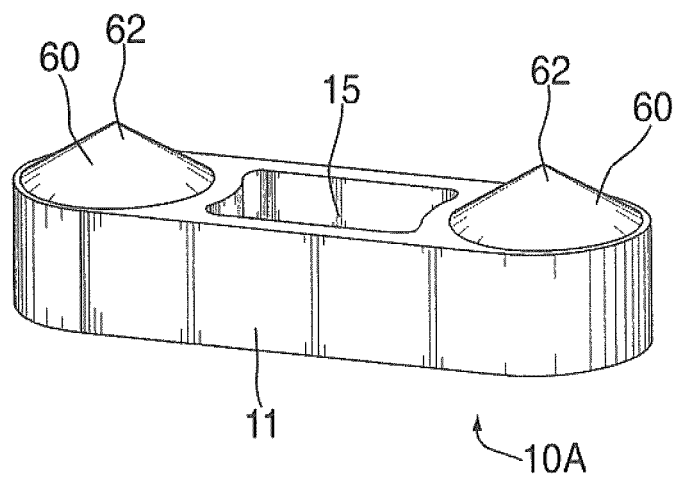

In a further aspect of the present invention, a piston/cylinder and locking arrangement as described above may be used to deploy extendable bone anchors. For example, implant 10A with conical bone engaging anchors 60 as shown in FIGS. 32A and 32B may be constructed with pistons 22 and cylinders 16 as described above in connection with implant 10 and shown, for example, in FIGS. 2, 3 and 4B. Implant 10A has a housing 11 as previously described and may include other previously described features such as interior cavity 15 for bone growth stimulating substances. However, in this embodiment, instead of upper interlocking endplate 13, the two pistons 22 individually terminate with conical bone engaging anchors 60. The bone engaging anchors, including sharp leading tip 62, form surface for engaging the vertebral body.

As shown in FIG. 32A, bone engaging anchors 60 are in a contracted configuration, within housing 11, to facilitate insertion of implant 10A. Using hydraulic actuation as previously described, bone engaging anchors 60 are moved to an extended configuration as shown in FIG. 32B, wherein at least leading tip 62 extends beyond housing 11 to engage and anchor in the bone. In order to ensure that the bone engaging anchors remain firmly engaged in the bone, locking mechanisms including multi-stepped upper and lower lock supports 17, 20 as previously described in connection with implant 10 and shown, e.g. in FIGS. 6A-12C, are provided to support each anchor 60 in the extended configuration. With this arrangement, the extended and locked anchor 60 helps to retain the implant in place.

Figure 33A:
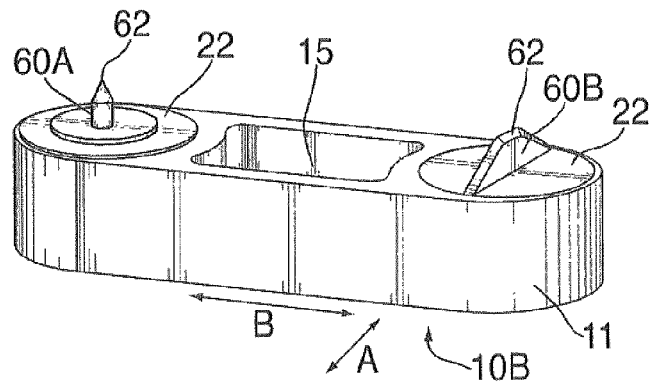
FIGS. 33A-C are perspective views showing alternative bone engaging anchors.
Figure 33B:
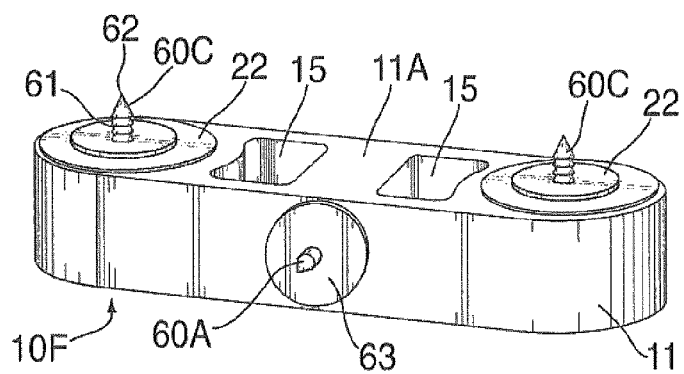
Figure 33C:
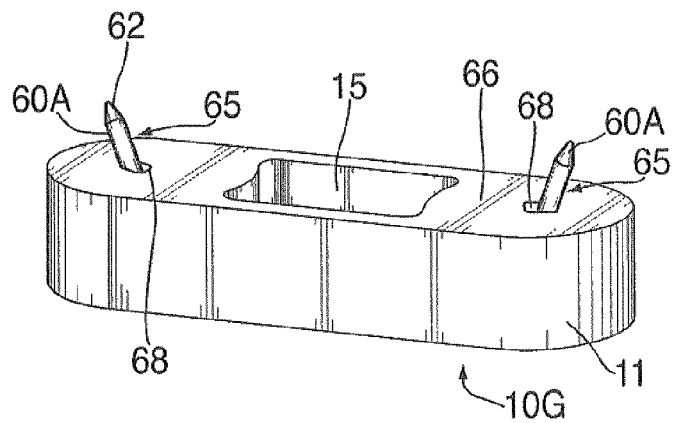

A variety of alternatives are possible for the bone engaging anchor according to the invention as illustrated in FIGS. 33A-C. For example, implant 10B in FIG. 33A includes bone engaging anchors formed as spike 60A and blade 60B. Blade 60B can be particularly effective in preventing motion along the insertion path after deployment. In this case, the length of the Blade 60B is aligned in the direction shown by arrow A. This is substantially orthogonal to the direction of implantation (arrow B) and would resist movement in that direction. Implant 10F, shown in FIG. 33B includes further possible variations. In this embodiment, the bone engaging anchors are formed as barbed spikes 60C. Barbs 61 along the shaft of the spikes resist forces that tend to move the tissue away from the implant along the axis of the anchor (much as the screw threaded anchor described below would also resist this force). Also included in implant 10F is a lateral bone engaging anchor 63 for anchoring in laterally oriented tissue. In the illustrated embodiment, lateral anchor 63 includes a plain spike 60A. Lateral anchor 63 is formed in the same manner and with the same components, i.e. piston, cylinder, locking mechanism, etc. as elsewhere described in this application, except that the components are oriented laterally as shown. To provide support for the bone anchor components in this lateral embodiment, housing 11 includes a central member 11A that divides interior cavity 15 into two portions. In the configurations of implants 10B and 10F, the top of piston 22 can also become a bone engaging surface when the anchor member is fully received within the bone. FIG. 33C shows a further alternative implant 10G, including anchors 65 extending obliquely from housing 11, rather than orthogonally. This oblique arrangement is helpful in resisting side to side rotational forces (for example when the patient/spine bends towards the side) and expansion forces. Once again, obliquely extending anchors 65 are essentially identical to other bone engaging anchors described herein except for the oblique orientation. Here, holes 68 are provided in top endplate 66 for the spikes to pass through. In general, bone engaging anchors according to embodiments of the invention should have a relatively small termination (e.g. tip 62) relative to the size of the piston diameter so that the force on the piston created by the hydraulic fluid is proportionally a much greater force at the small anchor termination to enhance its ability to extend into hard bony tissues. It will also be appreciated by persons skilled in the art that the various features of the bone engaging elements, e.g. spike, blade, barbs, etc., described herein may be combined in any desired combination, in addition to the exemplary combinations shown in the figures of the present application.

Figure 34A:
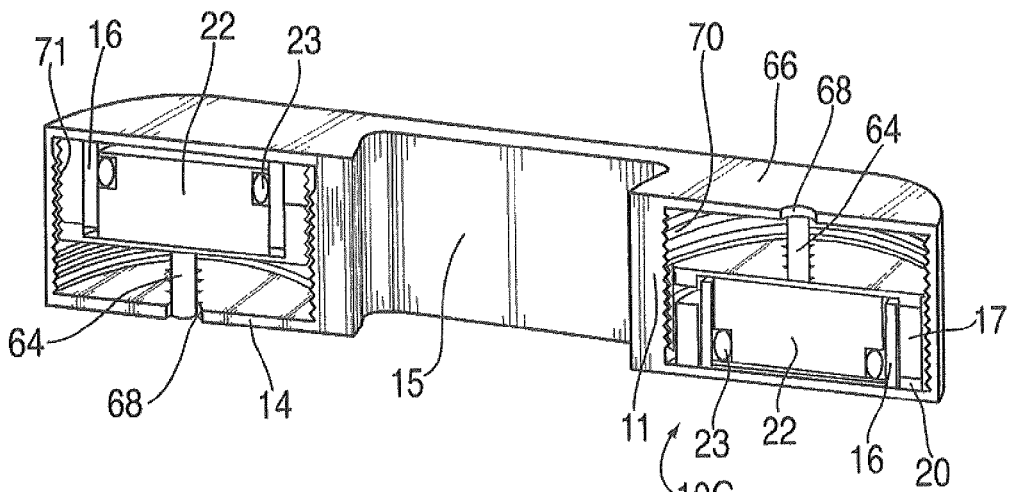
FIGS. 34A and 34B are perspective cross sectional views of another alternative embodiment of the present invention including locking, screw-threaded bone engaging anchors.
Figure 34B:
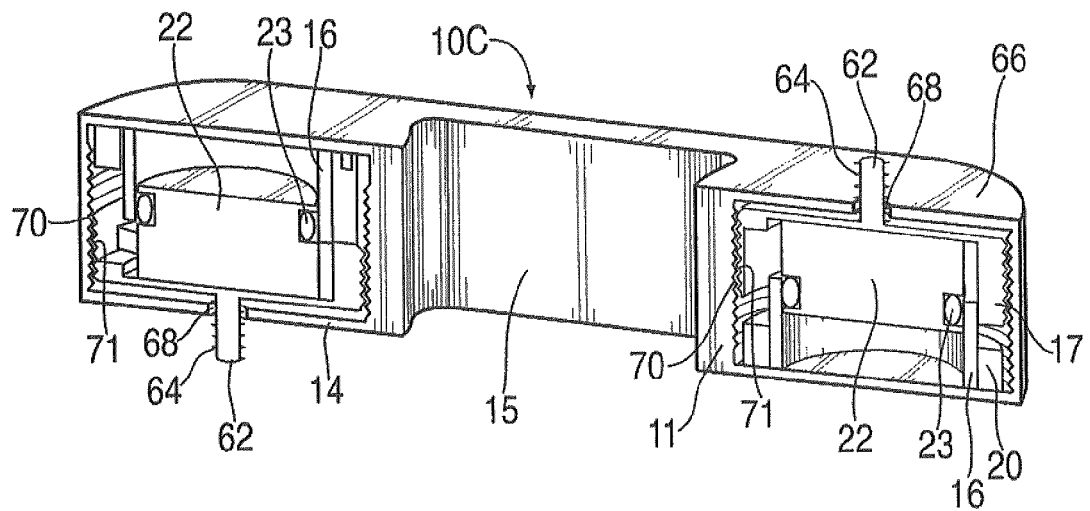

In another alternative embodiment, illustrated in FIGS. 34A and 34B, implant 10C includes screw-threaded members 64 as bone engaging anchors. Implant 10C also illustrates a further alternative wherein the bone engaging surfaces, such as the anchors, extend from opposite sides of the implant. In this exemplary embodiment, interlocking endplate 13 is replaced with an integrated top endplate 66. Holes 68 are provided for threaded member 64 to pass through. Persons of ordinary skill in the art will appreciate that holes 68 will be located as needed; in the illustrated embodiment one is in endplate 66 and the other in bottom endplate 14.

Threaded bone engaging anchors 64 extend outwardly from pistons 22. In order to rotate the threaded anchors into the bone when the pistons are extended, the inner wall of housing 11 is provided with a screw-threaded surface 70 that mates with corresponding threads 71 cooperating with pistons 22. As previously described, seals 23 act between the pistons 22 and cylinders 16 to prevent leakage of hydraulic fluid. When fluid is pressurized within the cylinders as described for prior embodiments, the piston is extended, but also driven in a circular motion by the engagement between threaded surfaces 70 and 71. The screw-threaded anchor 64 is thus driven into adjacent bone as extended.

Once again, locking mechanisms as previously described and shown, for example, in FIGS. 6A-12C, may be employed to prevent the bone engaging anchors from becoming unengaged from the bone. In the cross sectional views of FIGS. 34A and 34B, upper and lower lock supports 17, 20 are visible around the outside of the piston and cylinders. Alternatively, depending on the depth and pitch of the threaded portions, use of a separate locking mechanism may not be required. As persons of ordinary skill will appreciate, the configuration of the threads alone may be sufficient to prevent the anchors from backing out.

Figure 35A:
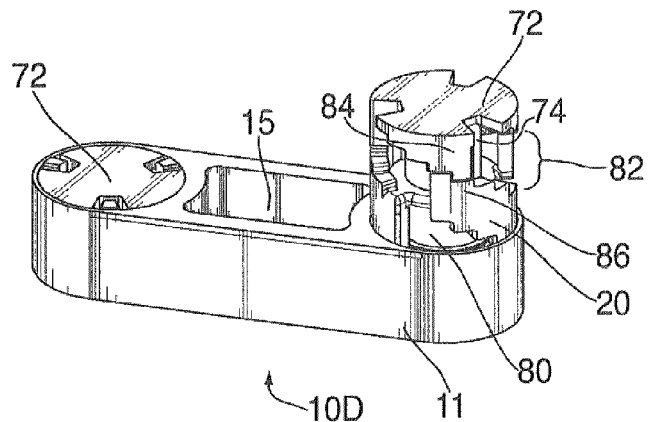
FIGS. 35A and 35B are perspective views of yet another embodiment of the present invention including locking, telescoping bone engaging surfaces.
Figure 35B:
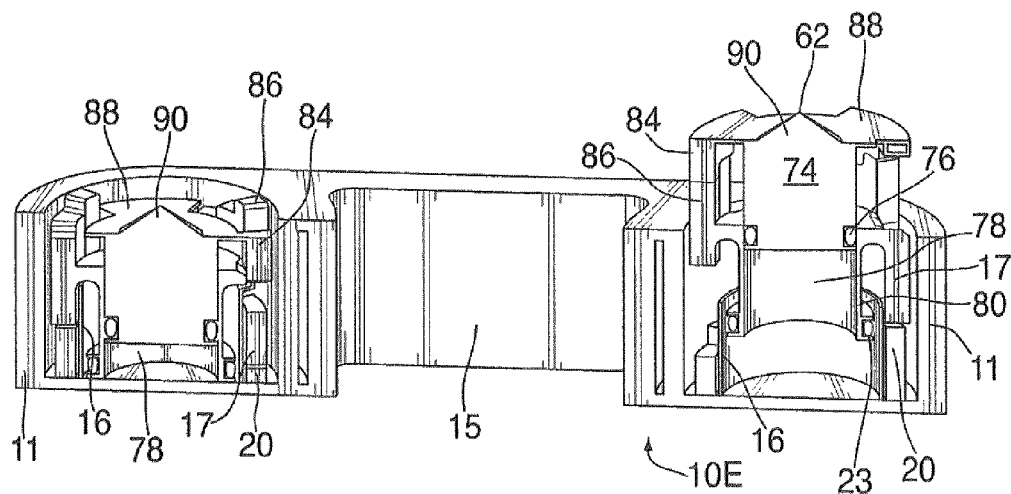

FIGS. 35A and 35B illustrate a further aspect of the present invention wherein locking mechanisms as described are utilized to secure telescoping bone engaging surfaces in place. As used herein, telescoping refers to nested, extendable members including at least one intermediate member between a base and bone engaging member.

Referring first to FIG. 35A, implant 10D has substantially planar bone engaging members 72. Bone engaging members 72 are thus similar to the bone engaging members of implant 10, but instead individually actuated without interlocking endplate 13. The piston/cylinder arrangement is also similar to that previously described except that here upper piston 74 is received in intermediate piston 80. Intermediate piston is in turn received in cylinder 16 as was previously described for piston 22. Upper piston 74 is sealed against intermediate cylinder 78 of intermediate piston by upper piston seals 76 (see FIG. 35B).

The telescoping bone engaging members 72 are secured by locking mechanisms in a similar manner to the earlier described embodiments, with the addition of an upper lock support 82 for the upper piston. Intermediate piston 80 is supported by upper lock support 17 and lower lock support 20 as previously described. Upper lock support 82 includes upper and lower lock supports 84, 86. Thus, upper piston 74 is secured to upper lock support 84 of the upper lock set. Lower lock support 86 of the upper lock set is mounted on top of upper lock support 17 of the lower lock set. One difference from the earlier described embodiments is that separate spring actuators 26 are not required for the upper lock set as they may be rotated along with the lower lock set by actuators 26.

Implant 10E, as shown in FIG. 35B includes a further variation in which the planar portion of upper bone engaging surface 88 is effectively annular with a conical anchor 90 at the center. Advantages of embodiments of the present invention including bone engaging anchors include the ability of the anchors to be extended lateral from the long axis of the implant (i.e., the insertion axis) with a relatively high force using the relatively small connection to the implant of the hydraulic line. This is an advantage over other methods that require larger access or larger connections to the implant for lager tools or non-hydraulic extension forces to extend the anchors into the hard, bony tissue.

A lateral cage implant, as illustrated for exemplary embodiments of the present invention herein, is particularly advantaged by the use of anchors as described herein because the lateral approach to the spine is a long and narrow approach, which limits the ability of the surgeon to use other instrumentation to extend anchors from the cage (as can be done more readily, for example, with an anterior approach where the access is not as narrow). However, as will be appreciated by persons of ordinary skill in the art, while particular, additional advantages may be presented in connection with the lateral approach and cages designed therefore, anchors according to embodiments of the present invention are advantageous for any approach as they can produce the required extension forces regardless of patient anatomy or other restrictions on the use of alternate extension means by the surgeon.

The description herein focused on the manner in which the locking elements are configured to lock the implant in extended configurations. Although this locking action resists the forces placed on the implant that would tend to force it back into a collapsed configuration that is not the only force the locking elements address. Once inserted between vertebral bodies the implant is subject to lateral forces and torsion moments as well as compressive forces. The locking features along with the other elements of the invention are designed to resist all of these forces to provide an implant that provides stable fixation and distraction.

A partial or complete discectomy is usually performed prior to the insertion of the spinal implant having features of the invention between vertebral bodies. The implant is introduced in its unexpanded state to enable it to be inserted posteriorly with minimal trauma to the patient and risk of injury to nerve roots. Once in place the implant can be expanded to provide both medial and lateral spinal correction. The implant has an unexpanded height of about 5 to about 15 mm, typically about 7 mm and is expandable to at least 130% to about 180% of the unexpanded height. Typically the implant is about 9 to about 15 mm wide, typically about 12 mm wide and about 25 to about 55 mm long, typically about 35 mm long to facilitate minimally invasive insertion and thereby minimize trauma to the patient and risk of injury to nerve roots.

Additional details of the implant such as the attachment of hydraulic lines and lines for transmission of a slurry or liquid bone graft material, device and hydraulic fluid delivery accessories and the like can be found in co-pending application Ser. No. 11/535,432 filed on Sep. 26, 2006 and Ser. No. 11/692,800, filed on Mar. 28, 2007, which are incorporated herein by reference.

It will be appreciated that the implant, including its various components should be formed of biocompatible, substantially incompressible material such as PEEK or titanium, and preferably type 6-4 titanium alloy or other suitable materials which will allow for long term deployment within a patient.

The extension of extendable members or pistons may be individually controlled so that the physician is able to provide a controlled angle of the corrective implant surface. While only two extendable members or pistons are described herein, the implant may be provided with three or more individually extendable members so that the physician can exercise three-dimensional control of the implant extension.

While the invention has been described in connection with what are presently considered to be the most practical and certain preferred embodiments, it is to be understood that the invention is not limited to the disclosed embodiments and alternatives as set forth above, but on the contrary is intended to cover various modifications and equivalent arrangements included within the scope of the following claims.

For example, the implants described herein are expanded by hydraulic fluid. Other expansion means may be employed. For example, a screw mechanism may be employed to expand the implant into engagement with adjacent vertebral surfaces. Further, the implant can be provided with load or pressure sensors that register differential pressure and pressure intensity exerted on the engaging surfaces of the SEC by the patient's vertebrae end plates to generate corrective signals, for example by computer control, that are used, e.g. by the surgeon or by a computer controlled mechanism to realign the patient's spine. The invention may further include a system that makes these adjustments, responsive to sensor signals, in real time and on a continual basis, such that the shapes of the implant changes to realign the patient's spine or mechanism. Preferably, such system is contemplated for use in setting the positions of the pistons during installation of the implant.

While particular forms of the invention have been illustrated and described herein, it will be apparent that various modifications and improvements can be made to the invention. Additional details of the spinal implant devices may be found in the patents and applications referenced herein. To the extent not otherwise disclosed herein, materials and structure may be of conventional design.

Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C §112(6) unless the following claims expressly use the terms "means for" or "step for" followed by a particular function without reference to a specific structure or a specific action. All patents and all patent applications referred to above are hereby incorporated by reference in their entirety.

What is claimed is:

1. A spinal implant for placement between first and second vertebral bodies, comprising:
   a. a first member having a surface for engaging an end of a first vertebral body;
   b. a second member having a surface for engaging an end of a second vertebral body;
   c. at least one extendable support element having a contracted configuration to facilitate deployment of the implant between the superior and inferior vertebral bodies and at least one extended configuration to extend the first member so that the surface thereof engages the end of the first vertebral body; and
   d. a locking system comprising a locking element that mechanically engages or interlocks with the extendable support element of the first member in a locked position to lock the implant between the first and second vertebral bodies in an expanded configuration, and a locking actuator disposed within the implant that moves the locking element into the locked position in response to deployment of the implant to said at least one extended configuration.

2. The spinal implant of claim 1 wherein the first surface for engaging an end of the first vertebral body includes a top end plate and the second surface for engaging an end of the second vertebral body includes a base plate.

3. The spinal implant of claim 2 wherein at least one top end plate cooperates with and is coupled to the extendable support element.

4. The spinal implant of claim 3 wherein the extendable support element is adapted to be extended by fluid.

5. The spinal implant of claim 4 wherein the fluid is an incompressible fluid.

6. The spinal implant of claim 2 wherein the at least one extendable member is a piston that engages the top plate.

7. The spinal implant of claim 6 including an internal cylinder configured to receive the piston.

8. The spinal implant of claim 7 including a source for fluid to extend the piston within the cylinder and raise the top plate.

9. The spinal implant of claim 7, wherein at least one said locking element is disposed within the cylinder.

10. The spinal implant of claim 6 including a pair of independently actuatable pistons which are rotatably interconnected to an articulating top plate.

11. The spinal implant of claim 1 wherein the locking system comprises a plurality of inter-engaging locking elements.

12. The spinal implant of claim 11 wherein one of the inter-engaging locking elements is a locking actuator configured to move the locking element into mechanical engagement or interlock with the extendable support element or first member after expansion of the expandable support member so as to lock the implant in an expanded configuration.

13. The spinal implant of claim 11 wherein one of the inter-engaging locking elements is an upper lock support member and another of the inter-engaging locking elements is a lower lock support member.

14. The spinal implant of claim 13 wherein the upper lock support member has a multi-stepped support surface and the lower lock support member has a multi-stepped support surface configured to engage the multi-stepped support surface of the upper lock support member.

15. The spinal implant of claim 14 including a locking actuator that is configured to effect relative motion between the upper and lower lock support members when the at least one extendable member is extended so as to lock the implant in an extended configuration by engaging the multi-stepped support surfaces of the upper lock support members and the lower lock support members.

16. The spinal implant of claim 15 wherein the multi-stepped support surface of the lower lock support member has an upper surface with a lock support stop which prevents over rotation of the arcuate lower lock support member.

17. The spinal implant of claim 14 wherein the lower and upper lock support members have arcuate shapes.

18. The spinal implant of claim 17 wherein the lower and upper lock support members have matching arcuate shapes.

19. The spinal implant of claim 18 wherein the arcuate shaped lower lock support member is disposed about a cylinder configured to receive a piston.

20. The spinal implant of claim 19 wherein the arcuate shaped upper lock support member is disposed about the piston and is secured to the top plate.

21. The spinal implant of claim 18 wherein the lock support members are circular.

22. The spinal implant of claim 21 wherein the circular lock support members have a plurality of multi-stepped support surfaces.

23. The spinal implant of claim 18 wherein the lower lock support member is disposed within the cylinder and the upper lock support member is within the piston.

24. The spinal implant of claim 15 wherein the locking actuator is a biased member configured to move one of the lock support members relative to the other.

25. The spinal implant of claim 24 wherein the biased member is a spring located in a groove in a base of the implant.

26. The spinal implant of claim 25 wherein the spring has a forward end configured to engage and rotate the lower lock support member when the implant is extended.

27. The spinal implant of claim 26 wherein the groove has an arcuate shape.

28. The spinal implant of claim 26 wherein the lower lock support member has a lower surface with a locking actuator transfer element configured to engage the forward end of the spring which effects rotation of the lower lock support member.

29. The spinal implant of claim 13 wherein the upper and lower lock support members are disposed between a pair of pistons and a pair of cylinders.

30. The spinal implant of claim 13 wherein a pair of upper and lower lock support members are disposed on opposite sides of a piston and cylinder.

31. The spinal implant of claim 13 wherein the upper lock support member is secured to the extendable member.

32. The spinal implant of claim 1 wherein the locking element which mechanically engages or interlocks with the expandable member or the first member directly applies a vertical force to the expandable member or the first member so as to lock the implant in the expanded configuration.

33. The spinal implant of claim 1 including a housing which contains at least in part the at least one extendable support element and the locking system.

34. The spinal implant of claim 1 wherein the locking element directly applies a vertical force to the extendable support element or the first member.

35. The spinal implant of claim 1, wherein the bone engaging surface of the first member comprises a bone anchor with a sharpened leading edge configured for anchoring into the bone.

36. The spinal implant of claim 35, wherein said bone engaging surface comprises a conically shaped member.

37. The spinal implant of claim 35, wherein said bone engaging surface comprises a spike.

38. The spinal implant of claim 35, wherein said bone engaging surface comprises a blade.

39. The spinal implant of claim 35, wherein said bone engaging surface comprises a screw threaded member.

40. The spinal implant of claim 35 wherein the bone anchor includes barbs.

41. The spinal implant of claim 1, further comprising:
   at least a second extendable support member having a contracted configuration to facilitate deployment of the implant between the first and second vertebral bodies and at least one extended configuration to extend the second member so that the surface thereof engages the end of the second vertebral body; and
   at least two locking elements, at least one each engaging or interlocking with each said extendable support element.

42. The spinal implant of claim 1, further comprising:
   at least one third member having a surface for engaging bony tissue of the vertebral body, said third member being oriented laterally with respect to the first and second members;
   at least a second extendable support element having a contracted configuration to facilitate deployment of the implant between the first and second vertebral bodies and at least one extended configuration to extend the third member so that the surface thereof engages a vertebral body; and
   at least two locking elements, at least one each engaging or interlocking with each said extendable support element.

43. The spinal implant of claim 1, wherein said at least one extendable support element comprises at least two telescoping members received within a base cylinder.

44. A spinal implant for placement between first and second vertebral bodies, comprising:
   a. a first member having a surface for engaging an end of a first vertebral body;
   b. a second member having a surface for engaging an end of a second vertebral body;

c. at least one extendable support element having a contracted configuration to facilitate deployment of the implant between the superior and inferior vertebral bodies and at least one extended configuration to extend the first member so that the surface thereof engages the end of the first vertebral body; and d. a locking system which has a locking element that mechanically engages or interlocks with the extendable support element of the first member to lock the implant between the first and second vertebral bodies in an expanded configuration; said spinal implant further comprising: at least two said first members; at least two said extendable support elements, one each supporting one of said first members; and at least two locking elements, at least one each engaging or interlocking with each said extendable support element or first member.

45. The spinal implant of claim 44, wherein said extendable support members are oriented act along separate, non-parallel axes.

46. The spinal implant of claim 44, wherein said at least two first members are joined by spaced apart elongate members to define a cavity surrounded by said elongate members and first members.

47. A spinal implant for placement between adjacent vertebral bodies, comprising:
   a. a top end plate for engaging an end of a first adjacent vertebral body;
   b. a bottom end plate for engaging an end of a second adjacent vertebral body;
   c. at least one extendable piston member having a contracted configuration within the implant to facilitate deployment of the implant between the first and second vertebral bodies and an extended configuration to extend the top end plate into engagement with the end of the first adjacent vertebral body;
   d. an upper lock support member having a multi-stepped support surface;
   e. a lower lock support member having a multi-stepped support surface configured to engage the multi-stepped support surface of the upper lock support member; and
   f. a locking actuator which causes relative motion between the upper and lower lock support members when the at least one extendable member is extended so as to lock the implant in an expanded configuration by engaging the multi-stepped support surfaces of the upper lock support members and the lower lock support members.

48. The spinal implant of claim 47 wherein the upper and lower lock support members have matching shapes which facilitate engagement of stepped support surfaces thereof.

49. The spinal implant of claim 48 wherein the upper and lower lock support members have matching arcuate shapes.

50. The spinal implant of claim 47 wherein a spring locking actuator is provided to move the lower lock support member toward the upper lock support when the at least one extendable member is extended.

51. The spinal implant of claim 47, wherein the bone engaging surface of the first member comprises a bone anchor with a sharpened leading edge configured for anchoring into the bone.

52. The spinal implant of claim 51, wherein the bone anchor includes barbs.

53. A spinal implant with hydraulically actuatable, locking bone anchors, comprising:
   an implant housing defining a cylindrical opening with an inner wall surface;
   a cylinder wall defining a cylinder disposed within said opening, the cylinder wall spaced from the inner wall surface of said opening to form an annular space therebetween;
   a hydraulic piston disposed within the circular opening and received within the cylinder, said piston having an outer end movable from a contracted position to an extended position;
   a bone engaging anchor including a screw member with bone cutting threads centrally disposed on the piston outer end and extending outward therefrom, said anchor being moveable with said outer end from a contracted position within said housing to an extended position out of said housing;
   inner wall screw threads disposed on at least a part of said inner wall surface;
   a piston flange extending from the piston outer end, over the cylinder wall and into said annular space;
   flange screw threads disposed on an outer surface of said piston flange and cooperating with the inner wall screw threads to rotate the bone engaging anchor in response to linear movement of the piston in the cylinder.

54. The spinal implant of claim 53, further comprising a locking mechanism for locking the bone engaging anchor in the extended position.

55. The spinal implant of claim 54, wherein said locking mechanism comprises:
   first, downward facing stepped engagement surfaces formed on the piston flange;
   an arcuate member with second, upward facing stepped engagement surfaces opposing and engaging the first stepped engagement surfaces; and
   a biasing element acting on said arcuate member and biasing said first and second stepped engagement surfaces in a contact direction.

56. A spinal implant with hydraulically actuatable, locking bone engaging surfaces, comprising:
   a housing defining at least one laterally spaced circular opening having a cylinder wall defining a base cylinder within said at least one circular opening, the cylinder wall being spaced from the housing to provide an annular space between the cylinder wall and housing;
   a first hydraulic piston disposed in said at least one opening, each said first piston having an outer end movable from a contracted position within said housing to an extended position out of said housing;
   an intermediate piston disposed between the first piston and the housing, each intermediate piston received within said base cylinder, and also defining an intermediate cylinder receiving the first piston therein;
   a bone engaging surface disposed at said first piston outer end; and
   a locking mechanism cooperating with said piston to lock the piston in the extended position, said locking mechanism including at least one locking member slidably disposed in said annular space.

57. The spinal implant of claim 56, wherein the locking mechanism comprises:
   an upper arcuate member with stepped engagement surfaces secured to the first piston and configured and dimensioned to be received in said annular space;
   a lower arcuate member with stepped engagement surfaces slideably disposed in said annular space;
   an intermediate arcuate member with upper and lower facing stepped engagement surfaces secured to the intermediate piston and configured and dimensioned to be received in said annular space with the upper engagement surfaces opposing and engaging the upper arcuate member engagement surfaces and the lower engagement surfaces opposing and engaging the lower arcuate member engagement surfaces; and a biasing element biasing acting on the lower arcuate member to cause engagement of said stepped engagement surfaces.

58. The spinal implant of claim 56, wherein said bone engaging surface comprises a bone engaging anchor having a sharp leading edge configured to penetrate bony tissue under the force of the piston.

59. The spinal implant of claim 56, further comprising at least two said circular opening with first pistons and intermediate pistons disposed therein.

* * * * *